(12) United States Patent
Guo et al.

(10) Patent No.: US 10,227,605 B2
(45) Date of Patent: Mar. 12, 2019

(54) POLYPEPTIDE REGULATING AND CONTROLLING THE FORMATION OF PLANT AGRONOMIC TRAIT OR YIELD TRAIT, AND USE OF POLYPEPTIDE

(71) Applicant: SHANGHAI INSTITUTES FOR BIOLOGICAL SCIENCES, CHINESE ACADEMY OF SCIENCES, Shanghai (CN)

(72) Inventors: Fangqing Guo, Shanghai (CN); Xiaoling Shang, Shanghai (CN); Hua Tian, Shanghai (CN)

(73) Assignee: SHANGHAI INSTITUTES FOR BIOLOGICAL SCIENCES, CHINESE ACADEMY OF SCIENCES (CN)

( * ) Notice: Subject to any disclaimer, the term of this patent is extended or adjusted under 35 U.S.C. 154(b) by 263 days.

(21) Appl. No.: 14/392,226

(22) PCT Filed: Jun. 24, 2014

(86) PCT No.: PCT/CN2014/080556
§ 371 (c)(1),
(2) Date: Dec. 24, 2015

(87) PCT Pub. No.: WO2014/206261
PCT Pub. Date: Dec. 31, 2014

(65) Prior Publication Data
US 2016/0230182 A1 Aug. 11, 2016

(30) Foreign Application Priority Data

Jun. 26, 2013 (CN) .......................... 2013 1 0259575

(51) Int. Cl.
*C12N 15/82* (2006.01)
*C12N 9/10* (2006.01)

(52) U.S. Cl.
CPC ....... *C12N 15/8261* (2013.01); *C12N 9/1048* (2013.01); *C12N 15/8218* (2013.01); *Y02A 40/146* (2018.01)

(58) Field of Classification Search
None
See application file for complete search history.

(56) References Cited

U.S. PATENT DOCUMENTS

2004/0268441 A1* 12/2004 Vance ................. C12N 15/821
800/288
2012/0023621 A1* 1/2012 Xing .................... C12N 9/0016
800/290

OTHER PUBLICATIONS

Fourgoux-Nicol et al., Plant Mol Biol 40:857-72 (1999).*
Wahl et al., Meth Enzymol 152:399-407 (1987).*
Hill & Preiss, Biochem Biophys Res Commun 244(2):573-77 (1998).*
Rhoads et al., J Biol Chem 273(46):30750-56 (1998).*
Guo et al., Proc Natl Acad Sci USA 101:9205-10 (2004).*
Guo et al., Curr Genom 17:476-89 (2016).*
Silverstone & Sun, Trends Plant Sci 5(1):1-2 (2000.*
Kim et al., Genom Biol 9:R45.1-15 (2008).*
Kellogg, Rice 2:1-14 (2009).*
Zhang, Curr Opin Plant Biol 6:430-40 (2003).*
Li & Sillanpaa, Trends Plant Sci 20(12):822-33 (2015).*
Castel & Martienssen, Nat Rev Genet 14:100-12 (2013).*
Klahre et al., Proc Natl Acad Sci (USA) 99(18):11981-86 (2002).*
Xu et al., Plant Physiol 142:429-40 (2006).*
Toru, K. et al.: "Cytokinin Activity of Cis-zeatin and Phenotypic Alterations Induced by Overexpression of Putative Cis-Zeatin-O-glucosyltransferase in Rice" Plant Physiology, vol. 160, No. 1, Sep. 30, 2012, p. 329, "Promoter-GUS Analysis" and "Generation and Characterization of Transgenic Plats Overexpressing cZOGT Genes in Rice".
Albert Pineda Rodo et al.: "Over-expression of a Zeatin 0-glucosylation Gene in Maize Leads to Growth Retardation and Tasselseed Formation" Journal of Experimental Botany, vol. 59, No. 10, May 31, 2008, p. 2673 "Abstract" and p. 2675, "Results".
Shandong University Master's Thesis, "Function analysis of a cytokinin O-glycosyltransferase gene in *Arabidopsis thaliana*", May 10, 2010, 74 pages.
NCBI Reference Sequence NP_001052346.1 Jun. 8, 2010.
English summary of the Shandong University Master's Thesis.

* cited by examiner

*Primary Examiner* — Russell T Boggs
(74) *Attorney, Agent, or Firm* — Banner & Witcoff, Ltd.

(57) ABSTRACT

The invention relates to a polypeptide for regulating agronomic characters and yield characters of plants and application thereof. The invention alters agronomic characters and yield characters of plants such as root development, tillering ability, heading period, panicle structure, grains number per panicle, grain morphology, and 1000 grains weight by directional regulating expression level of cytokinin-O-glycosyltransferase 1 in plants, thus achieve the aim of modifying plant type, panicle structure, grain morphology and weight, increasing yield.

3 Claims, 6 Drawing Sheets
(5 of 6 Drawing Sheet(s) Filed in Color)
Specification includes a Sequence Listing.

POLYPEPTIDE REGULATING AND CONTROLLING THE FORMATION OF PLANT AGRONOMIC TRAIT OR YIELD TRAIT, AND USE OF POLYPEPTIDE

RELATED APPLICATION INFORMATION

This application is a 371 of International Application PCT/CN2014/080556 filed 24 Jun. 2014, and which claims priority from Chinese Application No.: 201310259575.0 filed 26 Jun. 2013, the content of which is incorporated herein by reference.

TECHNICAL FIELD

The invention relates to the field of biotechnology; more particularly, a polypeptide for regulating the formation of main agronomic characters or yield characters of plants and application thereof.

TECHNICAL BACKGROUND

As global cultivated land decreases each year, crop yield is difficult to sustain human development. Although per mu yield of food crop is increasing, total output is difficult to maintain growth momentum. According to the report published by FAO, the world faces a big food crisis. Breed improvement of some main food crops and oil crops is extremely urgent.

Rice (*Oryza sativa* L.) is one of the important food crops in the world, more than half the world's population, including almost all of East and Southeast Asia, depends on rice as its principal staple food. Increasing rice yield is therefore significant for solving the problem of food security in the world. In general, direct factors affecting rice yield mainly include grain weight, grain number per spike, panicles per plant (similar to tillering number per plant), seed setting rate aspects. In addition, indirect factors such as plant height and tillering are also included. Thus, promoting increase in rice yield by changing these factors has broad application foreground in modern agricultural production.

Performing breed improvement by using biotechnology has gradually replaced traditional breeding, becoming a method for obtaining crops with high yield and good quality as well as economic crops, etc. Therefore, finding those acting genes for regulating plant related traits becomes the important premise for increasing crop yield by using biotechnology.

Consequently, the need for further developing new approaches applied to modify plants and make plants high-yielding is urgent in the field, so as to achieve directed improvement of plants such as crops, economic crops and flowers, and obtain new varieties of plants suitable for people's needs.

SUMMARY OF THE INVENTION

The object of the invention is to provide a polypeptide for regulating the formation of agronomic characters or yield characters of plants and application thereof.

In the first aspect of the invention, there is provided a method for regulating agronomic characters and/or yield characters of plants (e.g., crops), said method comprises: regulating the expression of cytokinin-O-glycosyltransferase 1 in plants.

In a preferred example, said plant is a gramineous plant; preferably, said gramineous plant is rice, wheat, corn, rye, sorghum; and/or said agronomic characters or yield characters include: root development, tillering ability, heading period, panicle structure, grains number per panicle, kernel morphology, and/or 1000 grains weight.

In another preferred example, said cytokinin-O-glycosyltransferase 1 is selected from the group consisting of (a) a polypeptide with an amino acid sequence set forth in SEQ ID NO: 3; (b) a polypeptide derived from (a), which is formed by one or more (such as 1-20; preferably, 1-10; more preferably, 1-5) amino acid residue substitutions, deletions or additions of the amino acid sequence of SEQ ID NO: 3 and has the function of (a) polypeptide; or (c) a polypeptide derived from (a), which shares more than 80% (preferably, 90%; more preferably, 95%; more preferably, 98%) homology with the polypeptide sequence defined by (a) and has the function of (a) polypeptide.

In another preferred example, said method comprises: reducing the expression of cytokinin-O-glycosyltransferase 1 in plants (such as crops); so as to increase plant's panicle length, primary branches, secondary branches and grains number per panicle; enhance plant seed's grain length, grain width, grain thickness and 1000 grains weight; promote plant's tillering ability; promote the growth of plant's stems and leaves; increase plant height; moderately delay senescence of flag leaf at filling stage; promote plant's root development and adventitious root formation; decrease plant's lateral root density; and/or reduce cZOG content in plants.

In another preferred example, said reducing the expression of cytokinin-O-glycosyltransferase 1 in plants comprises: transferring a down-regulator which down-regulates gene transcription, protein expression or protein activity of cytokinin-O-glycosyltransferase 1 to plant; preferably, said down-regulator is an interfering molecule specifically interfering with gene transcription of cytokinin-O-glycosyltransferase 1.

In another preferred example, said interfering molecule is dsRNA, antisense nucleic acid, small interfering RNA, microRNA targeting at inhibiting or silencing cytokinin-O-glycosyltransferase 1 coding gene or transcript thereof, or a construct able to express or form said dsRNA, antisense nucleic acid, small interfering RNA, microRNA; preferably, said interfering molecule is dsRNA or construct for which position 47-542 of SEQ ID NO: 1 is used as a silencing target.

In another preferred example, said interfering molecule contains the nucleotide sequence set forth in SEQ ID NO: 4 (i.e., position 47-542 of SEQ ID NO: 1).

In another preferred example, said interfering molecule is a construct containing the structure shown as formula (I):

$$\text{Seq}_{forward}\text{-X-Seq}_{reverse} \qquad \text{formula(I)},$$

in formula (I), $\text{Seq}_{forward}$ is the polynucleotide shown as SEQ ID NO: 4, $\text{Seq}_{reverse}$ is the polynucleotide complementary to $\text{Seq}_{forward}$;

X is a spacer sequence located between $\text{Seq}_{forward}$ and $\text{Seq}_{reverse}$, and said spacer sequence is not complementary to $\text{Seq}_{forward}$ and $\text{Seq}_{reverse}$.

In another preferred example, said method for reducing the expression of cytokinin-O-glycosyltransferase 1 in plants comprises:

(i) providing *Agrobacterium* carrying a vector which can interfere with gene expression, said vector is selected from the group consisting of:

(a) a vector containing cytokinin-O-glycosyltransferase 1 coding gene or gene fragment (antisense molecule) being promoted in the opposite direction;

(b) a vector containing an interfering molecule forming components specifically interfering with the expression (or transcription) of cytokinin-O-glycosyltransferase 1 coding gene in plants;

(ii) contacting tissues or organs of plants with *Agrobacterium* in step (i), so that said vector is transferred to tissues or organs of plants.

Preferably, said method further comprises:

(iii) selecting the tissue or organ of plants transferred with said vector; and (iv) regenerating the tissue or organ of plants in step (iii) into plants.

In another preferred example, said method for regulating agronomic characters and/or yield characters of plants (such as crops) comprises: increasing the expression of cytokinin-O-glycosyltransferase 1 in plants, so as to: increase plant's lateral root density; inhibit plant's root development and adventitious root formation; decrease plant height; inhibit the growth of plant's stems and leaves or tillering; accelerate plant's heading, flowering, filling or senescence; reduce plant's panicle length, primary branches, secondary branches or grains number per panicle; reduce plant seed's grain length, grain width, grain thickness or 1000 grains weight; and/or enhance cZOG content in plants.

In another preferred example, said method for increasing the expression of cytokinin-O-glycosyltransferase 1 in plants comprises: the polynucleotide encoding cytokinin-O-glycosyltransferase 1 is transferred to plant to get the plant transformed with said polynucleotide.

In another preferred example, said method for increasing the expression of cytokinin-O-glycosyltransferase 1 in plants comprises:

(S1) providing *Agrobacterium* carrying an expression vector which contains polynucleotide encoding cytokinin-O-glycosyltransferase 1;

(S2) contacting cells or tissues or organs of plants with *Agrobacterium* in step (S1), so that said polynucleotide is transferred to tissues, organs or seeds of plants.

In another preferred example, said method for increasing the expression of cytokinin-O-glycosyltransferase 1 in plants further comprises:

(S3) selecting the tissues, organs or seeds of plants transferred with said polynucleotide; and (S4) regenerating the tissues, organs or seeds of plants in step (S3) into plants.

In another aspect of the invention, there is provided use of cytokinin-O-glycosyltransferase 1 or coding gene thereof for regulating agronomic characters or yield characters of plants (such as crops).

In a preferred example, said cytokinin-O-glycosyltransferase 1 is selected from the group consisting of: (a) a polypeptide with an amino acid sequence set forth in SEQ ID NO: 3; (b) a polypeptide derived from (a), which is formed by one or more (such as 1-20; preferably, 1-10; more preferably, 1-5) amino acid residue substitutions, deletions or additions of the amino acid sequence of SEQ ID NO: 3 and has the function of (a) polypeptide; or (c) a polypeptide derived from (a), which shares more than 80% (preferably, 90%; more preferably, 95%; more preferably, 98%) homology with the polypeptide sequence defined by (a) and has the function of (a) polypeptide.

In another preferred example, said cytokinin-O-glycosyltransferase 1 coding gene contains the following sequence: SEQ ID NO: 1 or SEQ ID NO: 2 or degenerate sequence thereof.

In another aspect of the invention, there is provided use of cytokinin-O-glycosyltransferase 1 or coding gene thereof for serving as a molecular marker identifying agronomic characters or yield characters of plants (such as crops); preferably, said agronomic characters or yield characters include: root development, tillering ability, heading period, panicle structure, grains number per panicle, grain morphology, and/or 1000 grains weight.

In another aspect of the invention, there is provided use of a substance reducing the expression of cytokinin-O-glycosyltransferase 1, for regulating agronomic characters or yield characters of plants (such as crops); preferably, for: increasing plant's panicle length, primary branches, secondary branches and grains number per panicle; enhancing plant seed's grain length, grain width, grain thickness and 1000 grains weight; promoting plant's tillering ability; promoting the growth of plant's stems and leaves; increasing plant height; moderately delaying senescence of flag leaf at filling stage; promoting plant's root development and adventitious root formation; decreasing plant's lateral root density; and/or reducing cZOG content in plants.

In a preferred example, said substance reducing the expression of cytokinin-O-glycosyltransferase 1 is an interfering molecule specifically interfering with gene transcription of cytokinin-O-glycosyltransferase 1; preferably, said interfering molecule is dsRNA, antisense nucleic acid, small interfering RNA, microRNA targeting at inhibiting or silencing cytokinin-O-glycosyltransferase 1 coding gene or transcript thereof; preferably, said interfering molecule is dsRNA or construct for which position 47-542 of SEQ ID NO: 1 is used as a silencing target.

Other aspects of the present invention are apparent to those skilled in the art from the disclosure herein.

DESCRIPTION OF THE DRAWINGS

The file of this patent contains at least one drawing or photograph executed in color. Copies of this patent with color drawing(s) or photograph(s) will be provided by the Patent and Trademark Office upon request and payment of necessary fee.

DESCRIPTION OF THE PREFERRED EMBODIMENTS

Figure 1:
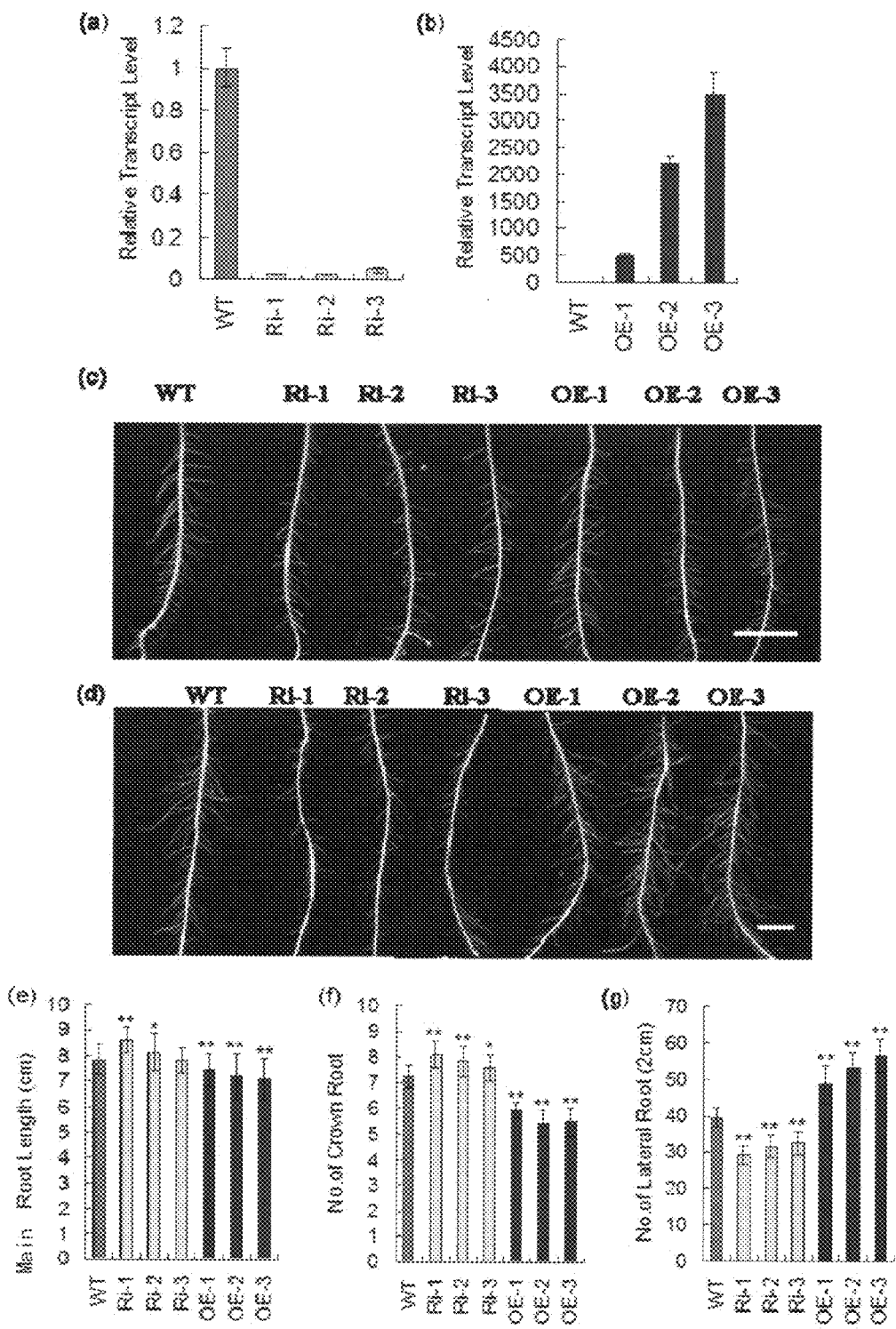
FIG. 1 shows phenotype analysis of the root of rice OsCOG1 RNAi lines and overexpression lines. (a-b): qRT-PCR analysis of rice OsCOG1 RNAi lines and overexpression lines. RNA of each strain in the experiment was from mixed sample of 10 individual leaves. (c): lateral root of seedlings grown hydroponically for 2 weeks. (d): lateral root of transgenic lines grown in field for about 4 weeks. (e-g): statistics about main root length, number of adventitious root and lateral root density of seedlings grown hydroponically for 2 weeks. Wherein, statistical method for lateral root is to perform statistics on the number of lateral root in which selected lateral root has fully grown and is within the 2 cm scope from base of the root. Making statistics on 10 single plants per line. Bar=1 cm.

After extensive and in-depth studies, the inventor isolated a cytokinin-O-glycosyltransferase 1 (CYTOKININ-O-GLUCOSYLTRANSFERASE1; COG 1) for the first time. By directional regulating expression level thereof in plants, agronomic characters and yield characters of plants (such as crops) such as root development, tillering ability, heading period, panicle structure, grains number per panicle, grain morphology, and 1000 grains weight may be significantly altered, thus achieve the aim of modifying plant type and panicle structure, increasing yield, etc.

As used herein, said "plant" may be a variety of crops, flower plants, or forestry plants and the like, including but not limited to grass family (e.g., *Oryza*). For example, said "plant" includes but not limited to rice, wheat, corn, barley, soybean, oilseed rape, cotton, etc.

The present invention also includes cytokinin-O-glycosyltransferase 1 fragments, derivatives and analogs. As used herein, term "fragment", "derivative" and "analog" refer to a polypeptide substantially remaining the same biological function or activity as cytokinin-O-glycosyltransferase 1 of the invention. The polypeptide fragment, derivative or analog of the invention may be (i) a polypeptide in which one or more conservative or non-conservative amino acid residues (preferably, conservative amino acid residues) are substituted, such substituted amino acid residues may or may not be encoded by genetic code, or (ii) a polypeptide having substituent groups in one or more amino acid residues, or (iii) a polypeptide formed by additional amino acid sequence fused to the polypeptide sequence (such as leader sequence or secretory sequence or a sequence used to purify this polypeptide or proteinogen sequence, or fused protein). These fragments, derivatives and analogs defined herein are well-known to those skilled in the art.

Any biologically active fragment of cytokinin-O-glycosyltransferase 1 can be used in the present invention. Herein, biologically active fragment of cytokinin-O-glycosyltransferase 1 means as a polypeptide, it still retains whole or part function of full-length cytokinin-O-glycosyltransferase 1. In general, said biologically active fragment retains at least 50% activity of full-length cytokinin-O-glycosyltransferase 1. Under more preferred condition, said active fragment can retain 60%, 70%, 80%, 90%, 95%, 99%, or 100% activity of full-length cytokinin-O-glycosyltransferase 1.

In the present invention, term "cytokinin-O-glycosyltransferase 1" refers to the polypeptide of SEQ ID NO: 3 sequence having the activity of cytokinin-O-glycosyltransferase 1. The term also includes variant forms of SEQ ID NO: 3 sequence having the same function as cytokinin-O-glycosyltransferase 1. These variant forms include but not limited to several (often 1-50, preferably 1-30, more preferably, 1-20, most preferably, 1-10, more preferably, such as 1-8, 1-5) amino acid deletions, insertions and/or substitutions, one or more (often within 20, preferably, within 10, more preferably, within 5) amino acid additions or deletions at C terminal and/or N terminal. For example, in the art, when substitutions are made by using amino acids with similar or resemble performance, protein function usually would not be changed. For example, adding one or more amino acids at C terminal and/or N terminal typically doesn't change protein function. The term further includes cytokinin-O-glycosyltransferase 1 active fragments and active derivatives.

Variant forms of the polypeptide include homologous sequence, conservative variant, allelic variant, natural mutant, induced mutant, protein encoded by DNA capable of hybridizing with cytokinin-O-glycosyltransferase 1_DNA under high or low stringent conditions. The present invention also provides other polypeptides, e.g., a fused protein containing cytokinin-O-glycosyltransferase 1 or fragment thereof.

Any protein having high homology with cytokinin-O-glycosyltransferase 1 (for example, having 70% or higher homology with the sequence shown as SEQ ID NO: 3; preferably, homology is 80% or higher; more preferably, homology is 90% or higher, such as 95%, 98% or 99% homology) and possessing the same function as cytokinin-O-glycosyltransferase 1 is also included in the present invention.

In the present invention, "cytokinin-O-glycosyltransferase 1 conservative variant polypeptide" refers to the polypeptide formed by at most 20, preferably, at most 10, more preferably, at most 5, most preferably, at most 3 amino acids replaced by amino acids with similar properties, compared with the amino acid sequence of SEQ ID NO: 3. It's best to produce these conservative variant polypeptides by amino acid substitution according to Table 1.

TABLE 1

| Amino acid residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also relates to polynucleotide sequences encoding cytokinin-O-glycosyltransferase 1 or conservative variant polypeptide, derivative thereof. Said polynucleotide may be in DNA or RNA form. DNA form includes cDNA, genomic DNA or synthetic DNA. DNA may be single-stranded or double-stranded. DNA may be a coding strand or non-coding strand. Coding region sequence encoding mature polypeptide may be the same as the coding region sequence shown as SEQ ID NO: 1 or SEQ ID NO: 2 or a degenerate variant. As used herein, "degenerate variant" in the present invention refers to the nucleic acid sequence which encodes the protein having SEQ ID NO: 3, but differs from the coding region sequence shown as SEQ ID NO: 1 or SEQ ID NO: 2. "Polynucleotide encoding polypeptide" may be the polynucleotide encoding said polypeptide, may also be the polynucleotide attached with coding and/or non-coding sequence.

The present invention also relates to variant of above-mentioned polynucleotide, which encodes polypeptide fragment, analog and derivative having the same amino acid sequence as the present invention. The polynucleotide variant may be a naturally occurring allelic variant or non-naturally occurring variant. These nucleotide variants include substituted variant, deleted variant and inserted variant. As is known in the art, allelic variant is a replacement form of polynucleotide, it might be one or more polynucleotide substitutions, deletions or insertions, but will not essentially alter the function of the polypeptide encoded.

The present invention also relates to a polynucleotide hybridizing with above-mentioned sequence and there is at least 50%, preferably, at least 70%, more preferably, at least 80% identity between the two sequences. The present invention particularly relates to a polynucleotide hybridizable with the polynucleotide according to the invention under stringent condition. In the present invention, "stringent condition" refers to: (1) hybridization and elution under relatively low ionic strength and high temperature, such as 0.2×SSC, 0.1% SDS, 60° C.; or (2) addition of denaturing agent when hybridizing, such as 50% (v/v) formamide, 0.1% fetal bovine serum/0.1% Ficoll, 42° C., etc.; or (3) hybridization which occurs only if identity between the two sequences is more than at least 90%, more preferably, more than 95%. Furthermore, hybridizable polynucleotide-encoded polypeptide has the same biological function and activity as the mature polypeptide shown as SEQ ID NO: 3.

It should be understood that cytokinin-O-glycosyltransferase 1 gene is preferably derived from rice, but other genes derived from other plants and highly homologous with rice cytokinin-O-glycosyltransferase 1 gene (e.g., having more than 80%, such as 85%, 90%, 95%, even 98% identity) are also included within the scope of the present invention. Methods and tools for comparing sequence identity are also well-known in the art, e.g., BLAST.

Full-length cytokinin-O-glycosyltransferase 1 nucleotide sequence of the present invention or fragment thereof can often be obtained by PCR amplification protocol, recombination method or synthetic method.

The present invention also relates to a vector containing said polynucleotide, and a host cell produced by genetic engineering using said vector or cytokinin-O-glycosyltransferase 1 coding sequence.

When said polynucleotide is expressed in higher eukaryotic cells, transcription will be enhanced if an enhancer sequence is inserted into the vector. The enhancer is a cis-acting element of DNA, normally has about 10-300 base pairs, acting on the promoter to enhance gene transcription. How to choose suitable vector, promoter, enhancer and host cell is apparent to those of ordinary skill in the art.

Transforming host with recombinant DNA can be performed by routine techniques well known to those skilled in the art. Transforming plants can use agrobacterium-mediated transformation or biolistic transformation and other methods, e.g., such as spraying method, leaf disc method, rice embryo transformation method, etc. Transformed plant tissues or organs can be regenerated into plants by conventional methods, so as to obtain the plant with changes of character.

The present invention provides use of said cytokinin-O-glycosyltransferase 1 or coding gene thereof, for regulating agronomic characters or yield characters of plants; or screening substances useful to regulate agronomic characters or yield characters of plants (i.e., said substance regulates agronomic characters or yield characters of plants via regulating the expression of cytokinin-O-glycosyltransferase 1). As a preferred mode, said cytokinin-O-glycosyltransferase 1 may be used to increase plant's panicle length, primary branches, secondary branches and grains number per panicle; enhance plant seed's grain length, grain width, grain thickness and 1000 grains weight; promote plant's tillering ability; promote the growth of plant's stems and leaves; increase plant height; moderately delay senescence of flag leaf at filling stage; promote plant's root development and adventitious root formation; decrease plant's lateral root density; and/or reduce cZOG content in plants.

The present invention also relates to up-regulator or down-regulator of cytokinin-O-glycosyltransferase 1 and use thereof. Since up-regulator or down-regulator of cytokinin-O-glycosyltransferase 1 can regulate the expression and/or activity of cytokinin-O-glycosyltransferase 1, etc., said up-regulator or down-regulator may also adjust agronomic characters or yield characters of plants by affecting cytokinin-O-glycosyltransferase 1, so as to achieve the aim of modifying plant.

Any substance able to increase the activity of cytokinin-O-glycosyltransferase 1, enhance its stability, promote its expression, extend its effective acting time, or promote its gene transcription and translation can be used in the present invention, as the substance used for regulating agronomic characters or yield characters of plants.

Any substance able to decrease the activity of cytokinin-O-glycosyltransferase 1, reduce its stability, inhibit its expression, decrease its effective acting time, or reduce its gene transcription and translation can be used in the present invention, as the down-regulator, antagonist or inhibitor of cytokinin-O-glycosyltransferase 1, such as the interfering molecule interfering with the expression of the cytokinin-O-glycosyltransferase 1 coding gene (e.g., the interfering molecule capable of forming microRNA). Said down-regulator, antagonist or inhibitor can be used to regulate agronomic characters or yield characters of plants. After obtaining the target sequence, the method for preparing an interfering molecule interfering with specific gene expression is well known to those skilled in the art.

The present invention also relates to a method for regulating agronomic characters or yield characters of plants, which comprises regulating the expression of cytokinin-O-glycosyltransferase 1 in said plant.

In one aspect, the present invention provides another method for regulating agronomic characters or yield characters of plants (e.g., crop), said method comprises: reducing the expression of cytokinin-O-glycosyltransferase 1 in plants (including making cytokinin-O-glycosyltransferase 1 not express or low in expression); so as to decrease plant's lateral root density; promote plant's root development and adventitious root formation; increase plant height; promote the growth of plant's stems and leaves or tillering; moderately delay plant's heading, flowering, filling or senescence; increase plant's panicle length, primary branches, secondary branches or grains number per panicle; enhance plant seed's grain length, grain width, grain thickness or 1000 grains weight; and/or reduce cZOG content in plants.

In another aspect, the present invention provides a method for regulating agronomic characters or yield characters of plants (e.g., crop), said method comprises: making said plant overexpress cytokinin-O-glycosyltransferase 1, so as to increase plant's lateral root density; inhibit plant's root development and adventitious root formation; decrease plant height; inhibit the growth of plant's stems and leaves or tillering; accelerate plant's heading, flowering, filling or senescence; reduce plant's panicle length, primary branches, secondary branches or grains number per panicle; reduce plant seed's grain length, grain width, grain thickness or 1000 grains weight; and/or enhance cZOG content in plants.

After knowing the use of said cytokinin-O-glycosyltransferase 1, various methods well known to those skilled in the art can be used for regulating the expression of said cytokinin-O-glycosyltransferase 1. For example, through approaches known to those skilled in the art, expression units (e.g., expression vector or virus, etc.) carrying cytokinin-O-glycosyltransferase 1 gene may be delivered to target site, and make it express active cytokinin-O-glycosyltransferase 1.

In addition, various methods well known to those skilled in the art can also be used for reducing the expression of cytokinin-O-glycosyltransferase 1 or resulting in loss of expression, for example, expression units (e.g., expression vector or virus, etc.) carrying cytokinin-O-glycosyltransferase 1 gene in reverse direction may be delivered to target site, making cell or plant tissue not express cytokinin-O-glycosyltransferase 1 or reduce the expression.

As an embodiment of the invention, cytokinin-O-glycosyltransferase 1 coding gene is cloned into a suitable vector by conventional methods, said recombinant vector carrying foreign gene is introduced to plant tissues or organs able to express said cytokinin-O-glycosyltransferase 1, making said plant express cytokinin-O-glycosyltransferase 1. By regenerating said plant tissues or organs into plants, obtain the plant overexpressing cytokinin-O-glycosyltransferase 1.

Preferably, there is provided a method for preparing a transgenic plant, comprises:

(1) exogenous cytokinin-O-glycosyltransferase 1 coding gene is transferred to plant organs or tissues to obtain the plant tissue, organ, or seed transformed with said gene; and (2) regenerating the plant tissue, organ, or seed transformed with exogenous cytokinin-O-glycosyltransferase 1 coding gene in step (1) into plants.

As a preferred example, said method comprises the steps:

(s1) providing *Agrobacterium* carrying an expression vector, said expression vector contains cytokinin-O-glycosyltransferase 1 coding gene;

(s2) contacting plant tissue, organ, or seed with *Agrobacterium* in step (s1), so that cytokinin-O-glycosyltransferase 1 coding gene is transferred into the plant, and integrated into chromosomes of plant cell;

(s3) selecting the plant tissue, organ, or seed transferred with cytokinin-O-glycosyltransferase 1; and (s4) regenerating the plant tissue, organ, or seed in step (s3) into plants.

Other methods for increasing the expression of cytokinin-O-glycosyltransferase 1 gene or homologous gene thereof are well known in the art. For example, the expression of cytokinin-O-glycosyltransferase 1 gene or homologous gene thereof may be enhanced driven by a strong promoter. Or the expression of cytokinin-O-glycosyltransferase 1 gene is increased by an enhancer (such as rice waxy gene first intron, Actin gene first intron and the like). Strong promoter suitable for the present invention includes but not limited to 35S promoter, Ubi promoter of rice, corn, etc.

Preferably, there is also provided a method for reducing the expression of cytokinin-O-glycosyltransferase 1 in plants, said method comprises:

(1) an interfering molecule interfering with the expression of cytokinin-O-glycosyltransferase 1 gene in plants is transferred to plant tissue, organ, or seed to obtain the plant tissue, organ, or seed transformed with said interfering molecule; and (2) regenerating the plant tissue, organ, or seed transformed with said interfering molecule in step (1) into plants.

As a preferred example, said method comprises the steps:

(i) providing *Agrobacterium* carrying a vector which can interfere with gene expression, said vector is selected from the group consisting of (c) a vector containing cytokinin-O-glycosyltransferase 1 coding gene or gene fragment (antisense molecule) being promoted in the opposite direction;

(d) a vector containing an interfering molecule forming components specifically interfering with the expression (or transcription) of cytokinin-O-glycosyltransferase 1 coding gene in plants;

(ii) contacting plant tissue or organ, or seed with *Agrobacterium* in step (i), so that said vector is transferred to the plant tissue or organ, or seed.

Preferably, said method further comprises:

(iii) selecting the plant tissue or organ, or seed transferred with said vector; and (iv) regenerating the plant tissue or organ, or seed in step (iii) into plants.

Other methods for reducing the expression of cytokinin-O-glycosyltransferase 1 gene or homologous gene thereof are well known in the art.

The present invention also includes plants obtained by using any forgoing method, said plant includes a transgenic plant transferred with cytokinin-O-glycosyltransferase 1 gene or homologous gene thereof; or a plant with reduced expression quantity (including low expression or no expression) of cytokinin-O-glycosyltransferase 1, etc.

Any suitable conventional means may be employed, including reagent, temperature, pressure condition and the like, to carry out said method.

Furthermore, the present invention also relates to using cytokinin-O-glycosyltransferase 1 or coding gene thereof as a tracing marker for progeny of gene transformed plant. The present invention also relates to using cytokinin-O-glycosyltransferase 1 or coding gene thereof as a molecular marker, identifying plant's root development, tillering ability, heading period, panicle structure, grains number per panicle, grain morphology, and/or 1000 grains weight by determining the expression of cytokinin-O-glycosyltransferase 1 in plants. Plant related characters related with cytokinin-O-glycosyltransferase 1 gene may also be used as an indication marker for true hybrid during hybrid seed production.

The present invention first discloses that important agronomic characters and yield characters such as plant's tillering ability, heading period, panicle structure, grains number per panicle as well as grain morphology and 1000 grains weight may be significantly altered by regulating the expression level of cytokinin-O-glycosyltransferase 1. Secondly, it discloses that other agronomic characters of rice may be regulated, including root development (the growth and development of adventitious root and axillary root) and leaf senescence, etc. Thirdly, it discloses that plant's root system structure and growth rate of the part above ground may be improved by regulating the expression level of cytokinin-O-glycosyltransferase 1.

Methods of the invention can tightly regulate plant's (crop) ability to form important yield characters, in which important agronomic characters and yield characters include but not limited to root system structure, plant height, tiller number, heading period, panicle structure, grains number per panicle, grain morphology and 1000 grains weight, etc. It's particularly important that using cytokinin-O-glycosyltransferase 1 provided by the present invention, the forming ability to simultaneously integrate three factors of characters (tiller number, grains number per panicle and 1000 grains weight) synergically positively regulating crop yield, has wide and important application prospect in increasing crop yield and modifying plant variety.

The application value of said cytokinin-O-glycosyltransferase 1 includes but not limited to the following aspects:

a. regulating endogenous active cytokinin level is achieved by adjusting rice endogenous cytokinin glycosylation level, so as to exert an effect on various aspects of plant growth. The advantage of the invention is that the regulation of the gene on endogenous cytokinin level is mild, from its phenotype in plant's RNAi lines and overexpression lines, changes of the gene expression level will not have a severe impact on plant's basic growth, thus plant variety may be improved by using the gene.

b. as widely used in plant genetic engineering, rice is one of the most important cereal crops in the world, increasing rice yield has a profound effect on safeguarding world food security. RNAi line of the invention may be significantly improved in yield, thus the purpose of increasing yield can be achieved by inhibiting the gene expression in rice using genetic engineering technology. Meanwhile, the protein of the invention may also regulate other growth and development processes of rice, based on the universal effect of cytokinin in plants, breed improvement can be performed on other plant varieties such as flower by the present invention.

c. the present invention may also be applied to the research field in plant science: cytokinin is an important plant growth regulator, the regulation of cytokinin metabolism involves a stringent and fine regulation process of endogenous active cytokinin level. The inventor's research on the function of cytokinin-O-glycosyltransferase 1 is important for further realizing the action mechanism of cytokinin in plants and disclosing the metabolism and regulation mechanism of cytokinin in plants.

The present invention is further illustrated by the following particular examples. It should be understood that these examples are merely used to illustrate the present invention, not to limit the scope of the invention. Experimental methods not indicating specific conditions in the following examples are often according to conventional conditions, such as conditions described in Molecular cloning: A Laboratory Manual, $3^{rd}$ edition, editor: J. Sambrook et al., Science Press, 2002, or conditions recommended by the manufacturer. Unless otherwise indicated, percentage and fraction are calculated by weight.

I. Materials and Methods (I) Plant Material

Rice material used in the example was *japonica* rice variety (*Oryza sativa* subsp. *japonica*) Zhonghua 11. The resultant T0 transgenic plant was cultivated in phytotron, culture condition was: 12 h light, 12 h dark; temperature=28° C. OsCOG1 RNAi and overexpression transgenic plant used in the experiment was planted in field, grown under natural conditions.

*Arabidopsis thaliana* material used in the example was ecotype Columbia (Col-0), cultivated in phytotron, culture condition was: 16 h light, 8 h dark; temperature=21° C. The resultant T1 plant from transgene was used for GFP fluorescence observation.

(II) Strain

1. *Escherichia coli*: DH5α: plasmid-transformed recipient bacterium.

2. *Agrobacterium tumefaciens*: EHA105: *Agrobacterium tumefaciens*, for genetic transformation of rice.

(III) Plasmid pMD19-T (Amp$^r$, TaKaRa, Dalian, China), for TA cloning.

pBlueScript SK: Amp$^r$, for in situ hybridization expression vector construction (Invitrogen).

pTCK303: Km$^r$ (strain) and Hyg$^r$ (plant), for construction of target gene RNAi expression vector (Wang, M. et al., Plant Molecular Biology Reporter 22, 409-417).

pHB: Km$^r$ (strain) and Hyg$^r$ (plant), for construction of target gene overexpression vector (Invitrogen).

p1300-GN: Km$^r$ (strain) and Hyg$^r$ (plant), for construction of promoter::GUS fusion expression vector (Invitrogen).

(IV) The Preparation and Transformation of *E. coli* Competent Cell

1. The Preparation of *E. coli* Super Competent Cell

Cryopreserved *E. coli* DH5α was taken to streak on LB plate, cultured overnight at 37° C. to grow single colony. 6 single colonies 2-3 mm in diameter were picked up and plated to 100 ml SOC liquid medium, cultured under 18° C., 150-250 rpm for 19-50 h to OD600=0.7-0.8, then ice-bath for 10 min. The bacterial solution was centrifuged for 10 min under 4° C. 4000 rpm, the supernatant was discarded, the thallus was collected, cells were suspended in ⅓ volume (approximately 30 ml) of ice-precooled TB solution (slowly shaking and suspending). The thallus was collected by recentrifugation, cells were suspended in 1/12.5 volume (approximately 8 ml) of ice-precooled TB solution (slowly shaking and suspending), slowly adding DMSO with 7% final concentration, again on ice-bath for about 10 min. Prepared competent cells were split charged into precooled EP tube, 50 ul per tube, stored in −80° C. refrigerator after liquid nitrogen flash freezing.

2. Plasmid Transformation of *E. coli*

Approximately 1 μg plasmid DNA was added to 50 μl DH5α competent cells, ice-bath for 30 min after blending; water-bath for 90 sec after taking out; ice-bath for 2 min; adding 800 μl LB liquid medium, cultured in shake flask for 1 hr under 37° C., 100 rpm; spread on LB plate containing 50 μg/ml corresponding antibiotic, cultured overnight at 37° C. to form single colony.

(V) The Preparation and Transformation of *Agrobacterium tumefaciens* Competent Cell 1. The Preparation of *Agrobacterium tumefaciens* Competent Cell EHA105 stored at −70° C. was taken to streak on the plate containing 50 μg/ml rifampin, cultured at 28° C. for 2 days. A single colony was picked up and plated to 5 ml LB liquid medium, shaking cultured for about 18 hr under 200 rpm, 28° C. 5 ml bacterial solution was transferred to LB liquid medium, shaking cultured to OD$_{600}$=0.5 under 28° C., 200 rpm. Transferred to 1.5 ml sterile EP tube, centrifuged at 5000 g for 5 min, the supernatant was discarded. Adding 1 ml precooled 0.1M CaCl$_2$ solution, cells were gently suspended, placed on ice for 20 min, centrifuged under 4° C., 5000 g for 5 min, and the supernatant was discarded. Adding 200 μl precooled 0.1M CaCl$_2$ solution containing 15% glycerol, gently suspended. Immediately cryopreserved at −80° C. after blending.

2. Plasmid Transformation of *Agrobacterium tumefaciens*

Approximately 1 μg plasmid DNA was added to 200 μl EHA105 competent cells, ice-bath for 30 min after blending; liquid nitrogen flash freezing for 5 min, water-bath for 5 min after taking out; ice-bath for 2 min; adding 800 μl LB liquid medium, cultured in shake flask for 3-5 hr under 28° C., 100 rpm; centrifuged at 7600 rpm for 30 sec after taking out, excess bacterial solution was removed and approximately 100 ul remained, the bacterial solution was well mixed, spread on LB plate containing 50 μg/ml corresponding antibiotic, cultured at 28° C. for 24-48 hr to form single colony.

(VI) Plasmid Mini Extraction (Alkaline Lysis Method)

1.5 ml culture solution was decanted into 1.5 ml EP tube, centrifuged under 4° C., 12000 g for 30 sec. The supernatant was discarded, the tube was inverted on toilet paper for several minutes, making liquid drain away. Bacteria precipitate was resuspended in 100 μl solution 1 (need vigorous shaking), placed at room temperature for 5-10 min. Adding newly formulated solution II 200 μl, fastening the tube, EP tube was rapidly gently reversed several times to well mix content (never shaking), ice-bath for 5 min. Adding 150 μl precooled solution III, fastening the tube and centrifuge tube was inverted, gently shaking for 10 sec, making the precipitate well mixed, ice-bath for 5-10 min, centrifuged under 4° C., 12000 g for 5-10 min. The supernatant was transferred to clean EP tube, adding equal volume of phenol/chloroform (1:1), shaked and mixed, centrifuged under 4° C., 12000 g for 5 min. The aqueous phase was removed to clean EP tube, adding 2 volumes of absolute ethanol, shaked and mixed prior to placed in −20° C. refrigerator for 20 min, then centrifuged under 4° C., 12000 g for 10 min. The supernatant was discarded, the tube was open and inverted on toilet paper to make all liquid drain away, adding 1 ml 70% ethanol to wash precipitate once, centrifuged under 4° C., 12000 g for 5-10 min. The supernatant was removed, the tube was inverted on toilet paper to make liquid drain away, vacuum dried for 10 min or dried at room temperature. The precipitate was dissolved in 30 μl ddH$_2$O, stored in −20° C. refrigerator until use.

(VII) Extraction of Plant Genomic DNA

Plant material was taken to put into EP tube, milled by oscillator after liquid nitrogen freezing. Adding 600 ul lysis buffer (0.2M Tris-HCl pH8.0, 7M urea, 2% Lauroyl Sarcosine Sodium, 0.05M EDTA) to milled powders and mixing. Adding 600 ul phenol/chloroform, vigorous shaking and mixing, centrifuged at 12000 rpm for 15 min, the supernatant was transferred to a new EP tube, adding 600 ul isopropanol, 60 ul 3M sodium acetate solution (pH5.2) and mixing, precipitated at −20° C. for 15 min, centrifuged at 12000 rpm for 15 min, the supernatant was discarded, the precipitate was washed by 75% ethanol, dissolved in 30 ul ddH$_2$O after precipitation and drying, stored in −20° C. refrigerator until use.

(VIII) Extraction of Plant Total RNA and Reverse Transcription

1. Extraction of Plant RNA

Plant material was taken to put into EP tube, milled by oscillator after liquid nitrogen freezing. Adding 1 ml Trizol to milled powders, (sample volume should not exceed 10% of Trizol solution volume) placed at room temperature for 5 min, (making ribonucleoprotein complex fully dissociate), adding 200 ul chloroform (per ml Trizol solution) and fastening cap, vigorous shaking (by hand) for 15 s, placed at room temperature for 2-3 min, centrifuged under 11000 g 4° C. for 20 min, the supernatant was transferred to a new RNAse free EP tube after centrifugation, adding 600 ul isopropanol and mixing, placed in −20° C. refrigerator for 30 min to precipitate RNA, centrifuged under 12000 g 4° C. for 20 min, the supernatant was removed, the precipitate was washed by 1 ml 75% ethonol (formulated by DEPC water), the supernatant was removed, the precipitate was blow-dried in super clean bench, dissolved in 30 ul RNAse free water (DEPC water).

2. Removal of DNA Contamination

| RNA | 20-50 ug |
| --- | --- |
| 10 × DNase I buffer | 5 ul |
| DNase I (RNase free) | 2 ul |
| RNase inhibitor (40 U/ul) | 1 ul |
| DEPC water | up to 50 ul |

Kept warm at 37° C. for 20-30 min.

After complete reaction, further added 50 ul DEPC water, 100 ul (equal volume) phenol/chloroform, well mixed, centrifuged under 12000 rpm 4° C. for 10 min, the supernatant was transferred to a new EP tube, added 10 ul 3M NaAC (ph 5.2), 250 ul (2.5 times) ice-cold absolute ethanol, precipitated at −20° C. for 30-60 min, centrifuged under 12000 rpm 4° C. for 15 min, washed by 70% ethanol, dried, dissolved in appropriate amount of water.

3. RNA Concentration Determination and Reverse Transcription 1 ul RNA was diluted 100 times to determine concentration, OD260/280 between 1.8-2.0 is appropriate, 2.0 is pure RNA, below 1.8 means containing protein. 2 ug RNA is taken to perform reverse transcription.

Reverse Transcription System:

| | |
|---|---|
| 5 × RT buffer | 4 ul |
| dNTP | 2 ul |
| RTAce | 1 ul |
| RNase inhibitor | 1 ul |
| Oligo d(T) | 1 ul |
| RNA | 2 ug |
| DEPC water | up to 20 ul |

Reverse Transcription Procedure:
30° C. 10 min→42° C. 1 h→95° C. 5 min→4° C. 10 min→end (IX) Construction of Vector
1. OsCOG1 Gene Overexpression Vector With rice cDNA as a template, specific primers OEF and OER (sequences see Table 2) were used to amplify rice OsCOG1 full-length CDS (including SEQ ID NO: 2), amplified fragment was ligated into pMD19-T vector, target fragment was ligated into binary vector pHB using restriction sites HindIII and XbaI after correct sequencing, OsCOG1 overexpression vector 3300E-pHB was constructed.

TABLE 2

| | Sequence | SEQ ID NO: |
|---|---|---|
| OEF | GT<u>AAGCTT</u>ATGCCCAGCGATGGCAGCTT | 5 |
| OER | GC<u>TCTAGA</u>TCAGCATTTCATGAGCATAA | 6 |
| RiF1 | CAGCTAGC<u>ATCGAT</u>GGAGAACCTCGAAGTCAA | 7 |
| RiR1 | GCAGATCT<u>ACTAGT</u>CCGCAGGAGACGAAGATG | 8 |
| RiF2 | CA<u>CCCGGG</u>GGAGAACCTCGAAGTCAA | 9 |

TABLE 2-continued

| | Sequence | SEQ ID NO: |
|---|---|---|
| RiR2 | CA<u>GGATCC</u>CCGCAGGAGACGAAGATG | 10 |
| InsF | GGCAGGCCGTTCATTTGG | 11 |
| InsR | TGTCCGCCTTCGCCGTAA | 12 |

2. OsCOG1 Gene RNAi Vector

With rice cDNA as a template, specific primers RiF1/RiR1 and RiF2/RiR2 were used to amplify a 496 bp in-length fragment in OsCOG1 full-length cDNA, respectively, amplified fragment was ligated into pMD19-T vector (Takara), forward and reverse target fragments were ligated into binary vector pTCK303 using restriction sites SpeI/ClaI and SmaI/BamHI after correct sequencing, respectively, OsCOG1 RNAi vector 330Ri-pTCK was constructed. The 496 bp in-length fragment has the following sequence (SEQ ID NO: 4):

```
  1 GGAGAACCTC GAAGTCAAAG AACAACGTGT TCACCATGCC CAGCGATGGC AGCTTCCGCA

61 TCGTCCTCTT CCCGTTCCCG GCGCAGGGCC ACTTCTCCGC CTTCCTCTCC CTCGCCGCCC

121 ACCTCCACGA CGCCCAGCCC ACGGCCGACA TCACCATCGT CTCCACCCCG CGCAACGTGG

181 AAGACCTCCG CCGCCGGTCG AGCTCCCAGA CGCGGTACCT CCGGTTCCAC GCCCTGCCGT

241 TCGCGCCAGC CGAGCACGGC CTGCCCGGAG ACATCGAGTC GACCGACGCC GTGCCGCTCC

301 TCCACTTCAT CACGCTGTTC GAGGCCACCG AGTCGCGCTC GCTACAGGAC AGCTTCGACA

361 GCTTCGTCCG TGACTTGATC ACCGACGCCG GAGCGGACGG TGCCAGGGTC TGCGTCATCG

421 CCGACCCCTT CCTCGCGTGG ACGACAGACG TCGCCCGCCG GCGTGGCGCC GCGCACGCCA

481 TCTTCGTCTC CTGCGG
```

3. In Situ Hybridization Expression Vector

With rice cDNA as a template, specific primers InsF and InsR were used to amplify a 427 bp fragment from OsCOG1 full-length cDNA, amplified fragment was ligated into pMD19-T vector (Takara), target fragment was ligated into pBluescript SK using restriction sites PstI and BamHI in pMD19-T vector after correct sequencing, respectively, thus in situ expression vector 330-pBSK was constructed. When synthesizing in situ hybridization probes, the vector was linearized using restriction sites EcoRI (antisense) and BamHI (sense), respectively, and antisense and sense probes were synthesized using T3 (antisense) and T7 (sense) polymerases (Roche).

(X) Rice Genetic Transformation

Genetic transformation methods for rice see Toki et al., The Plant journal: for cell and molecular biology 47, 969-976, and were partly adjusted based on this according to the actual situation.

1. Rice Seed Sterilization

Seeds were first soaked for 1 min by 75% ethanol, ethanol was removed, washed 2-3 times by sterile water, adding disinfectant with 1:3 volume ratio of sodium hypochlorite: water (adding one drop of Tween/50 ml solution), put in a shaker to sterilize for 45 min (160-165 rpm), washed again for 5 times by sterile water, excessive water was removed by sterile filter paper, mature seed was put into N6D medium (containing Pro), light culture at 32° C. for 1-5 d.

2. Culture of *Agrobacterium tumefaciens*

A single colony was picked from plate, inoculated into LB liquid medium containing corresponding antibiotic (pHB/pTCK303/p1300-GN/pBI101.2:GFP vector: 50 μg·ml-1Kan+50 μg·mL-1 Rif), shaked overnight in 28° C. shaker, then transferred to 50 mL same AB medium (containing corresponding antibiotic) in an amount of 2 ml, cultured for about 8 hr until the OD600 was approximately 0.5. Centrifuged under 4° C., 4000 rpm for 15 min, the thallus was collected. Then resuspended and precipitated using 50 mL AAM liquid medium containing 100 uM AS.

3: Transformation: Co-Culture of Callus and *Agrobacterium tumefaciens*

Thriving rice embryogenic callus was placed in sterile petri dish, soaked into fresh AAM *Agrobacterium tumefaciens* bacterial solution (containing 100 uM acetosyringone (AS)) and callus was taken out after 1.5 min, gently shaked for several times therein, bacterial solution was poured away, callus was placed in sterile filter paper, the residual bacterial solution was removed and air-dried, then transferred to cocultivation medium (N6D, containing 100 uM AS, without antibiotic), dark cultured at 25° C. for 3 d.

4. Screening

The callus was taken, and washed three times by sterile water containing 200 mg/L Timentin (T), until water was clear, washed once more by sterile water, excessive water was removed by filter paper, callus was placed in selection medium (containing 25 mg/L Hyg+100 mg/L T+Pro), light cultured at 32° C. for 2 weeks, observing anytime during the period, if *Agrobacterium tumefaciens* grows around the callus, then discarded, the callus without bacterium growth was quickly moved to new medium.

5. Differentiation

After screening, newly grown callus was grabbed by tweezer, moved to differential medium (containing 50 mg/L Hyg+100 mg/L T), light cultured at 26° C., replacing medium every two weeks until seedling grows from callus. The seedling was moved to rooting medium for rooting. It can be moved into soil to culture until new root grows out.

(XI) In Situ Hybridization

1. Tissue Fixation and Embedding

Using FAA (50% ethonol, 5% acetic acid, 3.7% formaldehyde) to fix materials, seems to be more thorough than fixed by 4% paraformaldehyde in evacuating. FAA fixing solution (400 ml): absolute ethanol 200 ml, glacial acetic acid 20 ml, 37% formaldehyde 40 ml, water (DEPC) 140 ml.

Day 1: Tissue Fixation

The Penicillin vial (the vial was preheated at 180° C.) charged with ⅔ volume of fixing solution was placed on ice, fresh material was taken and put into the vial, vacuum pumping on ice. Slowly pumping and keeping the vacuum for 15 min after bubbling, then slowly degassing, which was repeated several times until the material deposits on the bottom, in order to achieve rapid and thorough fixation. Replaced with fresh fixing solution, stayed overnight (12~16 hr) at 4° C.

Day 2: Dehydration

| Solution | Time |
| --- | --- |
| 50% ethonal | 60 min |
| 60% ethonal | 60 min |
| 70% ethonal | 60 min |

For all the above steps, ethonol was placed in 4° C. refrigerator after each replacing step, and gently shaked from time to time.

Day 3: Further Dehydration and Waxing

*All of the following steps are performed at 4° C. and gently shaked from time to time.

| Solution | Time |
| --- | --- |
| 85% ethonal | 60 min |
| 95% ethonal | 60 min |

*All of the following steps are performed at room temperature and gently shaked from time to time.

| Solution | Time |
| --- | --- |
| 100% ethonal | 30 min |
| 100% ethonal | 60 min |
| 25% xylene, 75% ethonal | 30 min |
| 50% xylene, 50% ethonal | 30 min |
| 75% xylene, 25% ethonal + safranine | 30 min |
| 100% xylene | 60 min |
| 100% xylene + ¼ volume Paraplast | overnight |
| Plus (paraffin) section | (never shaking) |

Preparatory work: Plus wax-scale (Paraplast Plus) was preheated at 60° C.

Day 4: Waxdip

The material was placed at 42° C. until wax block was completely melted. ¼ volume of wax block was added to complete melt, then removed to 60° C. Replaced with fresh melted wax liquid after a few hours, staying overnight.

Day 5-7: Waxdip

Replacing wax (Paraplast Plus) twice daily

Preparatory work: Regular wax-scale (Paraplast Regular) was preheated at 60° C.

Day 8: Embedding

Detailed steps and notifications see Guidance for paraffin section. Finally, the wax-scale embedding the material was stored at 4° C.

2. Section

A new glass slide was placed on Slide Warmers at 42° C., 1500 ul DEPC-$H_2O$ was added for uniform coverage. Cut wax ribbon floats on DEPC-$H_2O$ using tweezers, excessive water was removed by as much as possible by Kimwipe after 1-2 min when flattening the wax ribbon.

During the course of warming slide, the sections were examined with microscope quickly to find out the ideal section, which can save labor for slicing and slides. Finally, slides were remained on Slide Warmers at 42° C. overnight to make the slides stick.

3. Probe Synthesis

1) Probe Transcription:

Since the transcription efficiency of T7 polymerase is slightly higher than that of T3 polymerase, T7 should be used to transcribe antisense strand when constructing probe. 1.5 ml bacterial solution was dissolved in 30 ul dd$H_2O$ containing RNA enzyme after plasmid extraction according to the conventional alkaline method. Appropriate amount of plasmid was subject to enzyme digestion overnight to make it linear, carefully selecting an endonuclease with 5'-overhang terminal. Performing gel running to determine if enzyme digestion was complete. Extracting with phenol/chloroform twice to remove RNAse, finally dissolved in appropriate amount of DEPC-$H_2O$. It was better to cut gel to recover linear band, or it could be directly used as transcription template without recovery if enzyme digestion was determined to be relatively complete.

Transcription System (from Roche Kit)

| Template DNA | 2 ug |
| --- | --- |
| Transcription buffer | 2 ul |
| Nucleotides (mixture of UTP and dig-UTP) | 2 ul |
| RNASIN (RNAse inhibitor) | 1 ul |
| RNA dimer | 2 ul |
| DEPC-H$_2$O | up to 20 ul |

Kept warm at 37° C. for 2 hr.

1 ul gel was taken after transcription to determine the size and luminance of RNA bands, generally a total of about RNA 2 ug was synthesized after 2 hr. Replaced both the gel and electrophoretic buffer when detecting by gel running with new ones, electrophoresis time should not be too long to prevent RNA degradation.

80 ul DEPC-H2O, 1 ul 100 mg/ml tRNA and 5 Units DNAse were added and kept warm at 37° C. for another 10 min.

100 ul 4M NH4OAc and 400 ul absolute ethanol were added, −20° C. for 20 mins, maximum speed of rotation for 10 min, washed once by 70% and maximum speed of rotation for 10 min, blow-dried in super clean bench, had better not drying.

2) Alkaline Hydrolysis of Probe

Probes are generally hydrolyzed to 75-150 bp fragments, hydrolysis time was calculated according to the following formula:

$$T(\text{time}) = (L_i - L_f)/KL_iL_f$$

Li: the length of the original probe; Lf: the length of final hybridization probe; K=0.11 Kb/min In general, hydrolysis time of 500 bp probe was approximately 73 min.

Recovered RNA was dissolved in 100 ul DEPC-H2O, 100 ul 2× carbonate buffer (80 mM NaHCO$_3$, 120 mM Na$_2$CO$_3$) was added. Kept warm at 60° C. until the calculated time, 10 ul 10% acetic acid was added to stops reaction. 1/10 volume of 3M NaOAc (PH5.2) and two volumes of absolute ethanol were added, −20° C. for 20 mins. Finally, RNA was dissolved in 50% deionized formamide, the concentration was 1 ul/slide. In the final hybridization, the concentration of probe was 0.5 ng/ul/kb, hybridization system is 100 ul, if original probe is 500 bp, then each slide needs probe 0.5 ng×100 ul×0.5 Kb=25 ng. If the recovered probe is totally 1 ug in the end, it's dissolved in 40 ul 50% deionized formamide finally.

4. In Situ Hybridization

Specifically refers to the method used by Long, J. A. et al., Nature 379, 66-69.

(XII) RT-PCR and qRT-PCR Quantitative Analysis of OsCOG1

Rice ACTIN was used as reference gene for RT-PCR analysis. PCR reaction conditions were: 95° C. for 5 min; 95° C. for 30 sec, 57° C. for 30 sec, 72° C. for 30 sec, 28 cycles; 72° C. for 7 min; 4° C.

SYBR Premix Ex Taq™ II SYBR Premix Ex Taq™ kit from Takara was use to prepare the reaction system for qRT-PCR analysis, and was carried out on Real-time Fluorescent PCR Instrument iCycler (Bio-Rad), specific methods refer to instruction thereof. Rice ACTIN was used as reference gene, the primers used are listed in Table 3.

TABLE 3

| Primer Name | Sequence | SEQ ID NO: |
| --- | --- | --- |
| OsCOG1-RTF | AGCTTCGTCCGTGACTTGAT | 13 |
| OsCOG1-RTR | GTGGATGAGAAGCCCAATGT | 14 |
| OsACT-RTF | GAACTGGTATGGTCAAGGCTG | 15 |
| OsACT-RTR | ACACGGAGCTCGTTGTAGAAG | 16 |
| OsCOG1-qRTF | CCGTTCGGGTTTGACATCG | 17 |
| OsCOG1-qRTR | GTTCTTGGCACGCATCCTCTC | 18 |
| OsACT-qRTF | TGGTCGTACCACAGGTATTGTGTT | 19 |
| OsACT-qRTR | AAGGTCGAGACGAAGGATAGCAT | 20 |

(XIII) Determination of Rice Endogenous Cytokinin

The parts above ground of wild-type (WT), RNAi (Ri-1) and overexpression (OE-3) transgenic lines grown in soil for about 35 days were taken for analysis of endogenous cytokinin content, RNAi (Ri-1) and overexpression (OE-3) transgenic lines were both identified by qRT-PCR, 3 single plants per line were determined. Extraction of cytokinin referred to the method recorded by Dobrev, P. I. et al., Journal of chromatography. A 950, 21-29. Stable isotope labeled [$^2$H$_5$]ZOG was used as internal standard. High performance liquid chromatography-tandem mass spectrometry Agilent 6520 Accurate-Mass Q-TOF were used for cytokinin determination, chromatographic column was Zorbax XDB-C18, 4.6×50 mm, 1.8 um (Agilent). Water (containing 0.1% volume of formic acid) and methanol (B) were used as mobile phase. Liquid phase separation conditions are: 0 min, 92% A+8% B; 15 min, 85% A+15% B; 20 min, 10% A+90% B; 23 min, 10% A+90% B; 25 min, 92% A+8% B. Mean flow rate was 0.2 ml/min. Collision energy for tandem mass spectrometry (Collision energy) was 40V.

II Example

Example 1

OsCOG1 Regulates the Root Development in Rice

Plant root plays an important role in plant's fixation in soil, absorption of water and nutrients as well as ambient awareness and other aspects. It's known that rice's root is mainly composed of three root types, i.e., main root, lateral root and adventitious root. Previous studies conducted by the inventor showed that OsCOG1 was expressed in root tip and lateral root primordium and induced by auxin, thus presumably, the gene may be related with root development of rice. To verify the result, the inventor constructed OsCOG1 gene RNA interference (330Ri-pTCK) and overexpression (3300E-pHB) vectors and transformed them into *japonica* rice variety Zhonghua 11, finally screened 3 RNAi and 3 overexpression lines of OsCOG1. In 3 RNAi lines, the inhibitory effect of OsCOG1 gene was decreasing from Ri-1 to Ri-3; in 3 overexpression lines, the overexpression level of OE-1 was weak, while those of OE-2 and OE-3 were stronger (FIG. 1a, 1b). The inventor performed water culture on above 6 transgenic rice lines and made statistics about main root length, number of adventitious root and lateral root density of seedlings growing for 2 weeks.

Results showed that compared with wild type, main root length of RNAi lines slightly increased, number of adventitious root increased, but lateral root density significantly reduced, e.g., lateral root density of transgenic line Ri-1 seedling decreased nearly a quarter compared with wild type; while in overexpression lines, main root length reduced, number of adventitious root decreased and lateral root density significantly increased, e.g., lateral root density of transgenic line OE-3 seedling increased almost 1.5 times. It is noticeable that this change presented a certain correlation with the expression quantity of OsCOG1 gene (FIG. 1c, e-g).

Figure 2:
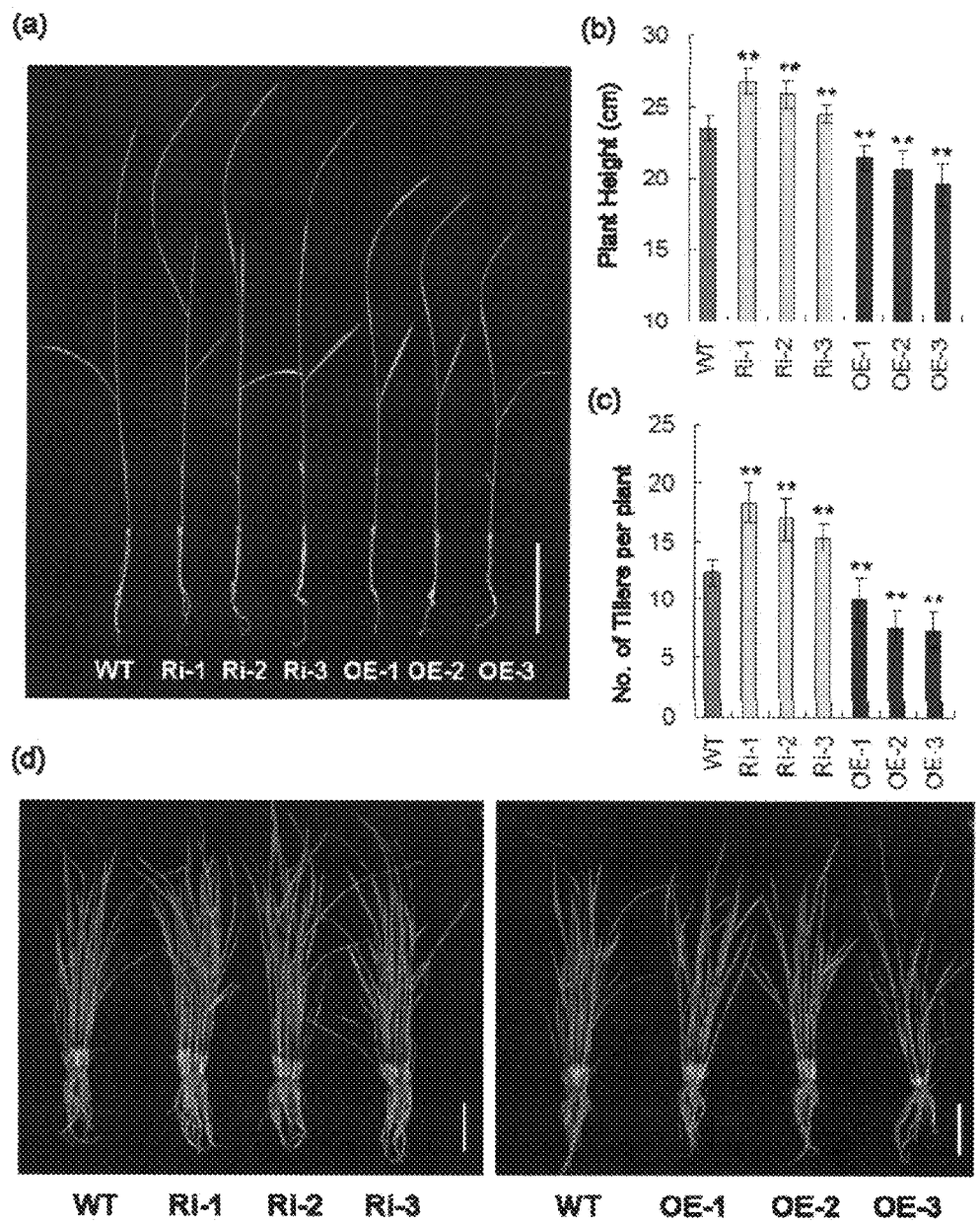
FIG. 2 shows phenotype observation and statistics of rice OsCOG1 overexpression lines and RNAi lines at seedling period. (a): plant height of wild-type, RNAi and overexpression transgenic seedlings germinated for 2 weeks (Bar=5 cm). (b): statistical results of seedling height in figure a. (n=10, P value<0.01, Student's t test). (c): statistical results of average primary tillering number of seedlings grown in field for 7 weeks. (n=10, P value<0.01, Student's t test). (d) seedlings grown in field for 7 weeks (Bar=10 cm).

Besides, the inventor also observed similar phenotype between RNAi and overexpression lines grown in field. For example, RNAi transgenic line growing for about 4 weeks also presented sparse lateral root, on the contrary, overexpression transgenic line had significantly denser lateral root (FIG. 1d); RNAi line growing for about 7 weeks had more developed root system and more adventitious root compared with wild type, while overexpression line growed significantly weaker and less in adventitious root (FIG. 2d).

In conclusion, the inventor considered that OsCOG1 played a key role in rice root development regulated by auxin.

Example 2

OsCOG1 Regulates Plant Height, Tillering, Flowering Phase and Leaf Senescence

Figure 4:
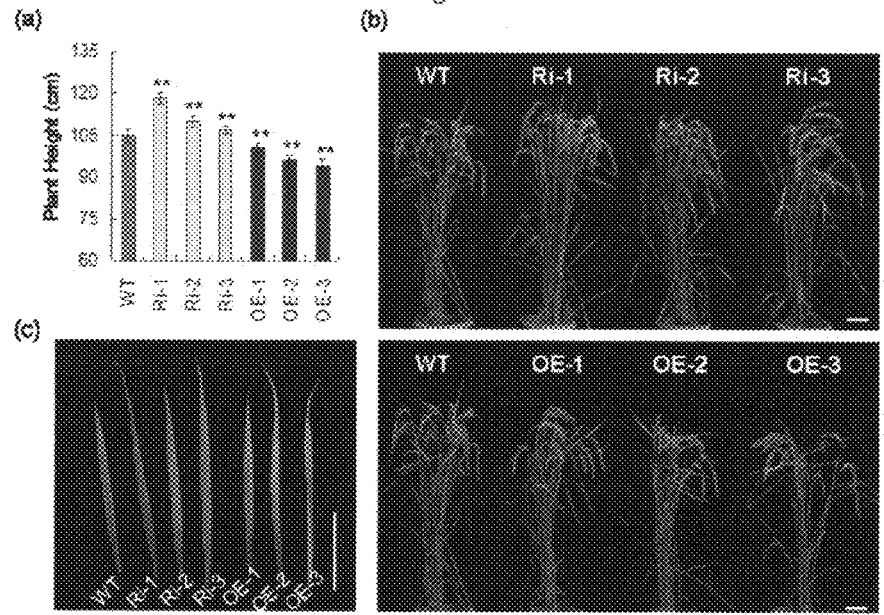
FIG. 4 shows phenotype observation and statistics of rice OsCOG1 RNAi lines and overexpression lines at late growth period. (a): statistics about average plant height of lines growing for 13 weeks. (n=20, **P value<0.01, Student's t test). (b): RNAi and overexpression lines growing for 14 weeks. (c): observation of flag leaf of overexpression and RNAi lines growing for 14 weeks. Bar=10 cm.
Figure 5:
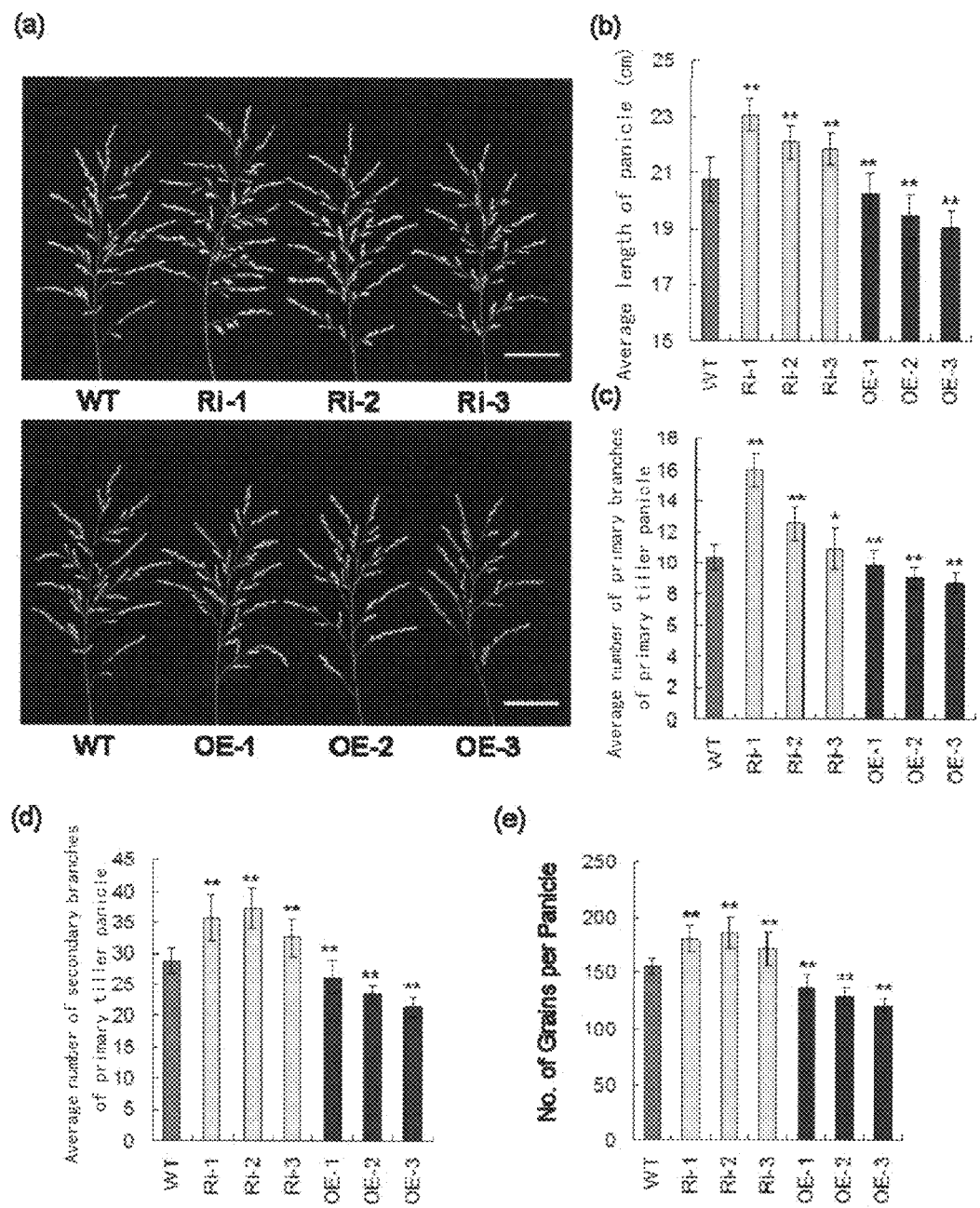
FIG. 5 shows statistics about characters of primary tiller panicle of rice OsCOG1 RNAi lines and overexpression lines. (a): primary tiller panicle of each line. Bar=5 cm; (b): average length of primary tiller panicle. (c): average number of primary branches of primary tiller panicle. (d) average number of secondary branches of primary tiller panicle. (e) grain number per panicle. (n=20, **P value<0.01, Student's t test)

In addition to root growth and development, OsCOG1 also affects rice's plant height, tillering, flowering time and leaf senescence. Compared with wild type, OsCOG1 transgenic line exhibited more obvious change in plant height, and this change presented a certain correlation with expression quantity of OsCOG1 gene. For example, rice seedling grown hydroponically for 2 weeks exhibited significant difference in plant height, compared with wild type, the part above ground of RNAi transgenic plant seedling was longer, while the part above ground of overexpression transgenic line was obviously shorter, and its plant height presented a negative correlation with expression quantity of OsCOG1 gene (FIG. 2a, b), which had the same trend in adult plant (FIG. 4a, b).

Figure 3:
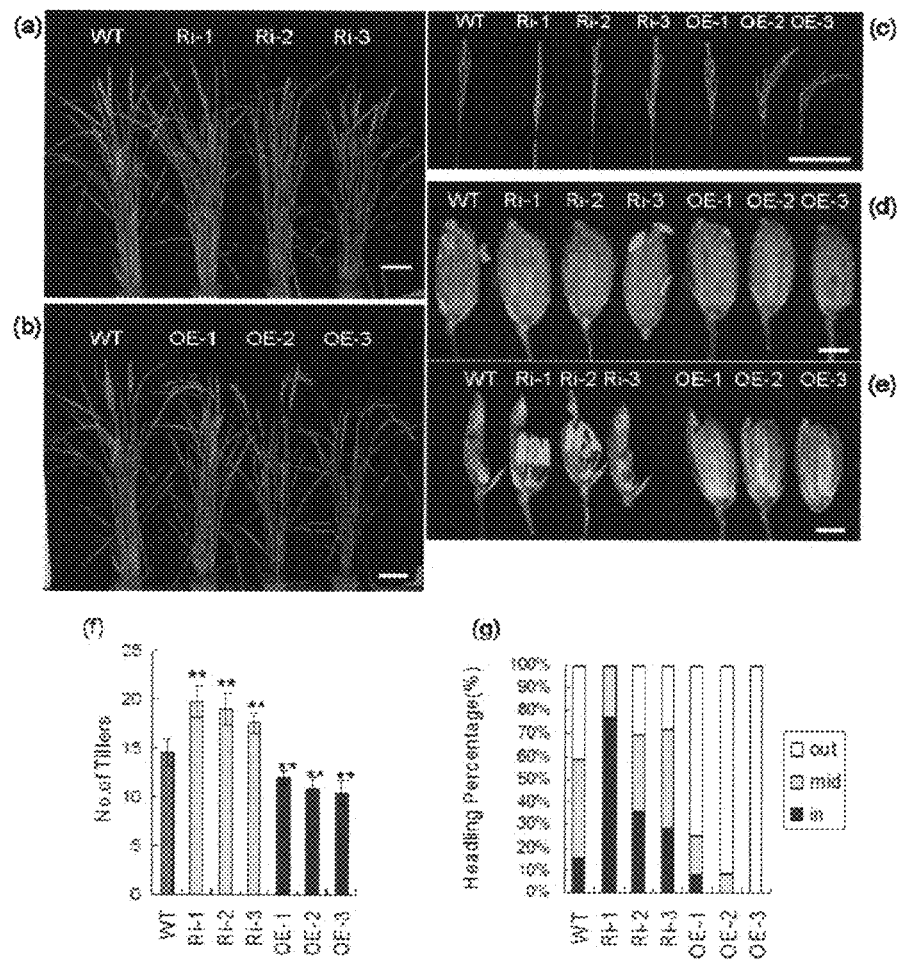
FIG. 3 shows phenotype observation and statistics of rice OsCOG1 overexpression lines and RNAi lines at heading period. (a-b): RNAi (a) and overexpression (b) lines grown in field for 10 weeks. Bar=10 cm (c): primary tiller panicle of each line at the same period. Bar=10 cm (d-e): apical spikelet status of each primary tiller panicle in figure (c). RNAi lines are at blooming stage, overexpression lines have already come into filling stage. Bar=2 mm (f): statistical results of average primary tillering number of overexpression lines and RNAi lines grown in field for 10 weeks. (n=20, **P value<0.01, Student's t test). (g): statistics about heading of lines grown in field for 10 weeks. Whether primary tiller panicle of each plant is headed is used as a standard, "out" denotes primary tiller panicle has been fully headed; "mid" denotes primary tiller panicle is partly headed; "in" denotes primary tiller panicle hasn't been headed. Percentage is calculated after performing statistics on 50 single plants per line.

Secondly, tillering ability of transgenic plant is also related with expression level of OsCOG1. The inventor made statistics about tillering status of each transgenic plant growing for 7 weeks and 10 weeks. Results showed that inhibition of OsCOG1 expression may significantly promote rice tillering; while overexpression of the gene had a certain inhibitory effect on tillering (FIG. 2c, d; FIG. 3f).

The above results shows that OsCOG1 gene plays a regulatory role in rice vegetative growth to a certain extent, overexpression of OsCOG1 inhibits the growth of rice's stems and leaves and tillering, while inhibition of the gene can facilitate the growth of rice's stems and leaves and tillering.

OsCOG1 gene also regulates rice's flowering time and leaf senescence. For example, compared with wild type, the heading to flowering stage of overexpression line promoted, while that of RNAi line delayed to some extent. The inventor made statistics about heading status of transgenic lines growing for 10 weeks, results showed that in this stage, wild type is at blooming stage, while overexpression line had come into filling, meanwhile, rice panicle of RNAi line had not headed or just headed (FIG. 3a-g).

On the other hand, in the late growth period, overexpression line presented premature senescence phenotype, overexpression plant's flag leaf turned yellow when growing at week 14, the tip of leaf became dead; on the contrary, RNAi plant's flag leaf still remained green (FIG. 4c).

The above results showed that OsCOG1 plays a role in regulating both flowering and leaf senescence in rice.

Example 3

OsCOG1 Regulates the Formation of Yield Characters of Rice

As an important food crop worldwide, rice's yield more or less affects many countries' economic development and food security, directly and indirectly. Generally speaking, factors affecting rice's yield mainly includes the following: 1) panicles per plant; 2) grain number per spike; 3) average grain weight, etc. In the characteristic aspect of panicles per plant, panicles per plant is closely related to tillering number per plant.

As shown in the above results, inhibition of OsCOG1 expression may increase tillering number per plant or panicles per plant in rice, while increasing expression quantity of OsCOG1 may decrease tillering number per plant or panicles per plant in rice (FIG. 3f). Secondly, in the characteristic aspect of grain number per panicle, panicle type, including panicle length and branch status, was an important factor determining grain number per panicle. The inventor investigated the panicle type of OsCOG1 in each RNAi and overexpression transgenic line, results indicated that panicle length, primary branches, secondary branches and grain number per panicle in RNAi line all significantly increased, while those of overexpression line significantly decreased, compared with wild type, the increasing or decreasing amount was at most about ¼-⅓ of wild type, meanwhile, this change presented a certain correlation with expression quantity of OsCOG1 gene (FIG. 5a-e).

Once more, in general, grain weight of rice depends on grain volume (size) and plumpness. The inventor measured grain length, grain width, grain thickness, length-width ratio of grain and 1000 grains weight in OsCOG1 RNAi and overexpression transgenic lines. Results showed that indexes such as grain length, grain width, grain thickness and 1000 grains weight in RNAi transgenic line were as high as about 1.1 times those of wild type; on the contrary, indexes such as grain length, grain width, grain thickness and 1000 grains weight in overexpression transgenic line were all less than wild type, the decreasing amount can at most reach about 1/10 of wild type, and this change presented a negative correlation with increase in expression quantity of OsCOG1 gene (FIG. 6b-f).

Figure 6:
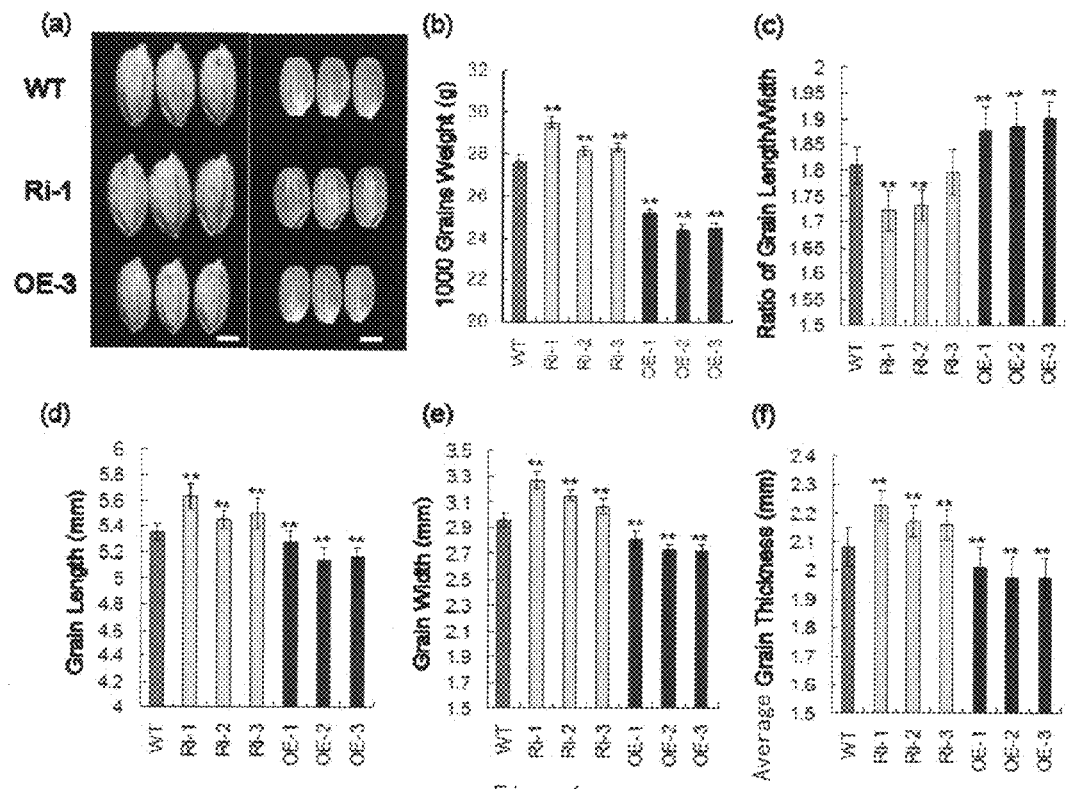
FIG. 6 shows statistics about grain characters of rice OsCOG1 RNAi lines and overexpression lines. (a) photograph of grain, Bar=2 mm; (b): 1000 grains weight; (c): length-width ratio of grain; (d): average grain length; (e) average grain width; (f) average grain thickness. (n=20, **P value<0.01, Student's t test)

In addition, the inventor also found that in grain shape, the grain was wider and rounder in RNAi transgenic line, while grain was thinner and longer in overexpression transgenic line, compared with wild type (FIG. 6a).

The above results indicates that OsCOG1 has certain influence on regulating panicle branching and grain development in rice, inhibiting the gene expression contributed to increase in rice yield.

Example 4

The Expression Pattern of OsCOG1 Gene in Rice

The inventor's study showed that the inhibition and overexpression of OsCOG1 gene both can lead to changes in root development, the growth of stems and leaves, tillering, plant height, panicle type and grain development and other aspects, therefore, in order to explore the function of OsCOG1 gene in rice, the inventor collected Zhonghua 11 wild-type rice materials at different growth and development stages to perform in situ hybridization analysis of OsCOG1 gene.

Figure 7:
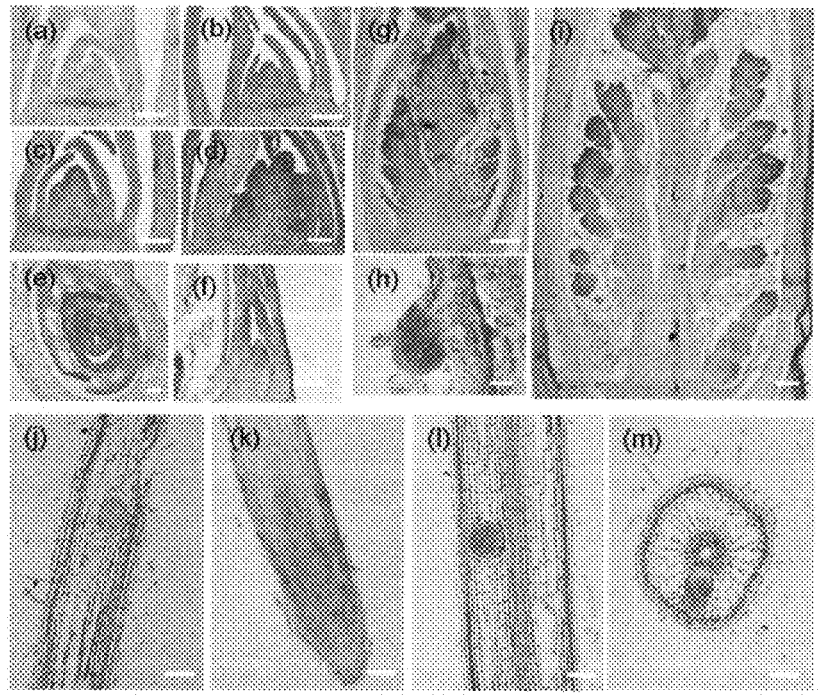
FIG. 7 shows in situ hybridization analysis of rice OsCOG1. (a): sense probe hybridization used as control. (b-c): shoot apical meristem (SAM). (d, g, i): inflorescence primodium at different developmental stages. (e): transection of seedlings above ground germinated for 4 days. (f): lateral bud. (h): adventitious root primordium. (j-m) in situ hybridization results of the root of rice seedling germinated for 4 days. OsCOG1 is mainly expressed in lateral root primordium (k), (l) and root tip (m). (j) is sense probe control. Bar=100 um
Figure 8:
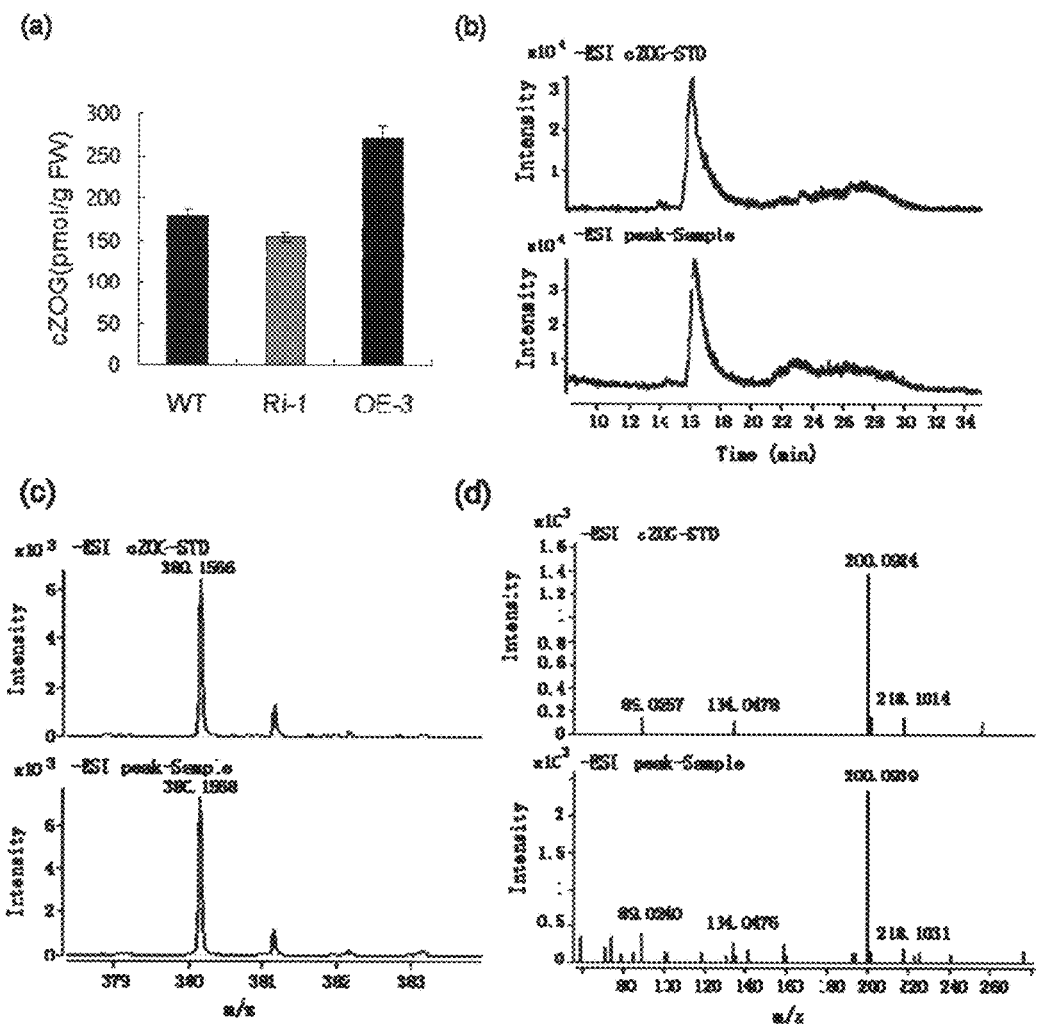
FIG. 8 shows determination results of endogenous cytokinin glycosides, cisZeatin-O-glucoside (cZOG) content in rice OsCOG1 RNAi lines and overexpression lines. (a): cZOG content in three lines (n=3). (b): chromatographic peak (HPLC) of cZOG standard and test sample. (c): mass spectrum (MS) of cZOG standard and test sample. (d) tandem mass spectrum (MS/MS) of cZOG standard and test sample.

Results were shown as FIG. 7, under normal growing conditions, for root part, OsCOG1 was mainly expressed in root tip, lateral root primordium and adventitious root primordium; while for the part above ground, mainly expressed in stem tip, lateral bud, leaf primordium and young leaf. This suggests that OsCOG1 has certain effect in growth and development of leaf, development of lateral root and adventitious root as well as growth of lateral bud, which is consistent with the observed result in RNAi and overexpression transgenic lines by the inventor.

In addition, since branching status of flower spike of OsCOG1 transgenic line also changed and no obvious abnormal morphology was seen in development of floral organ, the inventor thus assumed that OsCOG1 might play a certain role in early differentiation and development of rice inflorescence. To verify this presumption, the inventor performed in situ hybridization analysis of inflorescence at different stages of early differentiation and development. Results indicated that in primary branch and secondary branch differentiation period of inflorescence, OsCOG1 was strongly expressed in vigorously differentiated and developed primordium tip (FIG. 7), but correspondingly, primary branch and secondary branch significantly decreased in OsCOG1 overexpression line, while branch increased in RNAi line. This result suggested that OsCOG1 expression can inhibit differentiation of primary branch and secondary branch in rice flower spike.

Example 5

OsCOG1 Regulates Cytokinin Glycosylation Level of Rice Cell

Zeatin is a main cytokinin having biological activity in plants, its content more or less directly affects the realization of biological function of cytokinin. Based on prediction, OsCOG1 is a —O-glycosyltransferase of cytokinin, which is responsible for performing glycosylation modification of active cytokinin in vivo to make it temporarily inactive. Meanwhile, OsCOG1 RNAi and overexpression transgenic lines also exhibited cytokinin-related phenotype in many aspects. Therefore, to verify if these changes in OsCOG1 transgenic line are related with changes in cytokinin glycosylation level in vivo, above ground growing part from seedlings growing for about 35 days of two lines Ri-1 and OE-3 in RNAi and overexpression transgenic lines were used to determine the content of endogenous cytokinin glucoside trans-Zeatin-O-glucoside (tZOG), cis-Zeatin-O-glucoside (cZOG). Results showed that cZOG content significantly increased in overexpression plant OE-3.

The above results showed that OsCOG1 played an important role in regulating endogenous cytokinin glycosylation level in rice.

All documents mentioned in the present invention are incorporated by reference in the application, as if each document is individually incorporated by reference. In addition, it should be understood that after reading the above teachings of the present invention, those skilled in the art can make various modifications or changes of the present invention, and these equivalents fall within the scope of the application defined by the appended claims.

The invention claimed is:

1. A method for regulating agronomic characteristics and/or yield characteristics of a plant, wherein said method comprises: regulating expression of cytokinin-O-glycosyltransferase 1 in the plant;

wherein said cytokinin-O-glycosyltransferase 1 is SEQ ID NO: 3;

wherein said regulating comprises: transferring to the plant a down-regulator which down-regulates the expression of said cytokinin-O-glycosyltransferase 1, so as to: increase the plant's panicle length, primary branches, secondary branches and grain number per panicle; enhance the plant's seed's grain length, grain width, grain thickness and 1000-grains weight; promote the plant's tillering ability; promote the growth of the plant's stems and leaves; increase the plant's height; moderately delay senescence of the plant's flag leaf at filling stage; promote the plant's root development and adventitious root formation; decrease the plant's lateral root density; and/or reduce cis-zeatin-O-glucoside (cZOG) content in the plant;

wherein said plant is a gramineous plant; and wherein said down-regulator is a construct able to express or form a dsRNA, said construct consisting of the nucleotide sequence set forth in SEQ ID NO: 4.

2. The method according to claim 1, wherein said gramineous plant is rice.

3. The method according to claim 1, wherein transferring said down-regulator comprises:

(S1) providing an Agrobacterium carrying an expression vector which contains a polynucleotide encoding the down-regulator; and (S2) contacting tissues, organs, or seeds of the plant with the Agrobacterium in step (S1), so that said polynucleotide is transferred to the tissues, organs or seeds of the plant.

* * * * *

SEQUENCE LISTING

<160> NUMBER OF SEQ ID NOS: 20

<210> SEQ ID NO 1
<211> LENGTH: 1719
<212> TYPE: DNA
<213> ORGANISM: Oryza sativa

<400> SEQUENCE: 1

```
ggcttcctct cctttcagac aaagcaaaaa tttaatttcc ttccagtgga gaacctcgaa      60
gtcaaagaac aacgtgttca ccatgccag cgatggcagc ttccgcatcg tcctcttccc      120
gttcccggcg cagggccact tctccgcctt cctctccctc gccgcccacc tccacgacgc      180
ccagcccacg gccgacatca ccatcgtctc caccccgcgc aacgtggaag acctccgccg      240
ccggtcgagc tcccagacgc ggtacctccg gttccacgcc ctgccgttcg cgccagccga      300
gcacggcctg cccggagaca tcgagtcgac cgacgccgtg ccgctcctcc acttcatcac      360
gctgttcgag gccaccgagt cgcgctcgct acaggacagc ttcgacagct tcgtccgtga      420
cttgatcacc gacgccggag cggacggtgc cagggtctgc gtcatcgccg accccttcct      480
cgcgtggacg acagacgtcg cccgccggcg tggcgccgcg cacgccatct tcgtctcctg      540
cggcgcgttc ggcagcgtgg tgttccactc gctgtggaac cacttgccgc acctgcgtgc      600
gcccggtgac gacgcgttct gcctcccgga ccacccggag gttactgtcc accggtcgca      660
gcttccgcct tacctactcc acgccgacgg cacggaccgg tggtcggccc accaccgccg      720
gcagacatcg gccgggtacg acaccgacgc gattctcatc agcacgatgg aggagttgga      780
gacgaccggg ctgcgcatgc tccggaaaac gatgggcgtc ccggtctatc ccatcggccc      840
```

```
tctagtgcgt cgccggacgg agcactccga tcacatcggt gaccataacg acgatgacgt    900
caagcggtgg ctcgacaccc gagaggagag gtcagtgctg tacatctcat tcgggtctaa    960
taactcgcta aggcctgacc agatggttga cctcgccatg gcactggagc tcaccggcag   1020
gccgttcatt tgggctatcc gtccgccgtt cgggtttgac atcgagacca caacggccg    1080 cgagttcagc gccgagtggt tgccggaagg gttcgaggag aggatgcgtg ccaagaacat   1140
tgggcttctc atccacgggt gggctccgca ggtgagcatc ctcgcgcacg cgtccaccgg   1200
cgcgttcctg agccactgcg gctggaactc tgtgctggag agcatggcgc acggcgtgcc   1260
aatcatcgcg tggccgctca cggcggacca gttcttcaac gcccagatgc tggaggagtg   1320
gggcgcgtgc gtggaggtgt cccgcgggaa ctggccggac tccccggcgc tggagcgtga   1380
gagggtggtc gaggtcgtgg agatggtgat ggggattacg gcgaaggcgg acaagatacg   1440
acagagtgtg aagcagattc aggggatgat tggtcgaact ctggaggacg gtggttcgtc   1500
caagacagca ttggaggaat tcttgaagct gcatggtcac attatgctca tgaaatgctg   1560
acgccgagag aaataatttt ctgttttagc aatttgccca accttgaaac gtggtgcctg   1620
aaataaccta ttatgtgttc ttgaataacg cacgcatttg ggttttgtat tggaaaagct   1680
aatttcgcaa gaaggttaat acacaacagc tatagcatt                           1719
```

<210> SEQ ID NO 2  
<211> LENGTH: 1479  
<212> TYPE: DNA  
<213> ORGANISM: Oryza sativa

<400> SEQUENCE: 2

```
atgcccagcg atggcagctt ccgcatcgtc ctcttcccgt tcccggcgca gggccacttc     60
tccgccttcc tctccctcgc cgcccacctc cacgacgccc agcccacggc cgacatcacc    120
atcgtctcca ccccgcgcaa cgtggaagac ctccgccgcc ggtcgagctc ccagacgcgg    180
tacctccggt tccacgccct gccgttcgcg ccagccgagc acggcctgcc cggagacatc    240
gagtcgaccg acgccgtgcc gctcctccac ttcatcacgc tgttcgaggc caccgagtcg    300
cgctcgctac aggacagctt cgacagcttc gtccgtgact tgatcaccga cgccggagcg    360
gacggtgcca gggtctgcgt catcgccgac cccttcctcg cgtggacgac agacgtcgcc    420
cgccggcgtg cgccgcgca cgccatcttc gtctcctgcg cgcgttcgg cagcgtggtg     480 ttccactcgc tgtggaacca cttgccgcac ctgcgtgcgc ccggtgacga cgcgttctgc    540
ctcccggacc accggaggt tactgtccac cggtcgcagc ttccgcctta cctactccac    600
gccgacggca cggaccggtg gtcggcccac caccgccggc agacatcggc cgggtacgac    660
accgacgcga ttctcatcag cacgatggag gagttggaga cgaccgggct cgcatgctc     720 cggaaaacga tgggcgtccc ggtctatccc atcggccctc tagtgcgtcg ccggacggag    780
cactccgatc acatcggtga ccataacgac gatgacgtca gcggtggct cgacacccga   840 gaagagaggt cagtgctgta catctcattc gggtctaata actcgctaag gcctgaccag    900
atggttgacc tcgccatggc actggagctc accggcaggc cgttcatttg ggctatccgt    960
ccgccgttcg ggtttgacat cgagaccacc aacggccgcg agttcagcgc cgagtggttg   1020
ccggaagggt tcgaggagag gatgcgtgcc aagaacattg gcttctcat ccacgggtgg    1080 gctccgcagg tgagcatcct cgcgcacgcg tccaccggcg cgttcctgag ccactgcggc   1140
tggaactctg tgctggagag catggcgcac ggcgtgccaa tcatcgcgtg gccgctcacg   1200
```

-continued

```
gcggaccagt tcttcaacgc ccagatgctg gaggagtggg gcgcgtgcgt ggaggtgtcc      1260
cgcgggaact ggccggactc cccggcgctg gagcgtgaga gggtggtcga ggtcgtggag      1320
atggtgatgg ggattacggc gaaggcggac aagatacgac agagtgtgaa gcagattcag      1380
gggatgattg gtcgaactct ggaggacggt ggttcgtcca agacagcatt ggaggaattc      1440
ttgaagctgc atggtcacat tatgctcatg aaatgctga                            1479
```

<210> SEQ ID NO 3
<211> LENGTH: 492
<212> TYPE: PRT
<213> ORGANISM: Oryza sativa

<400> SEQUENCE: 3

```
Met Pro Ser Asp Gly Ser Phe Arg Ile Val Leu Phe Pro Phe Pro Ala
1               5                   10                  15

Gln Gly His Phe Ser Ala Phe Leu Ser Leu Ala Ala His Leu His Asp
            20                  25                  30

Ala Gln Pro Thr Ala Asp Ile Thr Ile Val Ser Thr Pro Arg Asn Val
        35                  40                  45

Glu Asp Leu Arg Arg Arg Ser Ser Ser Gln Thr Arg Tyr Leu Arg Phe
    50                  55                  60

His Ala Leu Pro Phe Ala Pro Ala Glu His Gly Leu Pro Gly Asp Ile
65                  70                  75                  80

Glu Ser Thr Asp Ala Val Pro Leu Leu His Phe Ile Thr Leu Phe Glu
                85                  90                  95

Ala Thr Glu Ser Arg Ser Leu Gln Asp Ser Phe Asp Ser Phe Val Arg
            100                 105                 110

Asp Leu Ile Thr Asp Ala Gly Ala Asp Gly Ala Arg Val Cys Val Ile
        115                 120                 125

Ala Asp Pro Phe Leu Ala Trp Thr Thr Asp Val Ala Arg Arg Arg Gly
    130                 135                 140

Ala Ala His Ala Ile Phe Val Ser Cys Gly Ala Phe Gly Ser Val Val
145                 150                 155                 160

Phe His Ser Leu Trp Asn His Leu Pro His Leu Arg Ala Pro Gly Asp
                165                 170                 175

Asp Ala Phe Cys Leu Pro Asp His Pro Glu Val Thr Val His Arg Ser
            180                 185                 190

Gln Leu Pro Pro Tyr Leu Leu His Ala Asp Gly Thr Asp Arg Trp Ser
        195                 200                 205

Ala His His Arg Arg Gln Thr Ser Ala Gly Tyr Asp Thr Asp Ala Ile
    210                 215                 220

Leu Ile Ser Thr Met Glu Glu Leu Glu Thr Thr Gly Leu Arg Met Leu
225                 230                 235                 240

Arg Lys Thr Met Gly Val Pro Val Tyr Pro Ile Gly Pro Leu Val Arg
                245                 250                 255

Arg Arg Thr Glu His Ser Asp His Ile Gly Asp His Asn Asp Asp Asp
            260                 265                 270

Val Lys Arg Trp Leu Asp Thr Arg Glu Glu Arg Ser Val Leu Tyr Ile
        275                 280                 285

Ser Phe Gly Ser Asn Asn Ser Leu Arg Pro Asp Gln Met Val Asp Leu
    290                 295                 300

Ala Met Ala Leu Glu Leu Thr Gly Arg Pro Phe Ile Trp Ala Ile Arg
305                 310                 315                 320

Pro Pro Phe Gly Phe Asp Ile Glu Thr Thr Asn Gly Arg Glu Phe Ser
```

```
            325                 330                 335
Ala Glu Trp Leu Pro Glu Gly Phe Glu Arg Met Arg Ala Lys Asn
        340                 345                 350
Ile Gly Leu Leu Ile His Gly Trp Ala Pro Gln Val Ser Ile Leu Ala
        355                 360                 365
His Ala Ser Thr Gly Ala Phe Leu Ser His Cys Gly Trp Asn Ser Val
    370                 375                 380
Leu Glu Ser Met Ala His Gly Val Pro Ile Ile Ala Trp Pro Leu Thr
385                 390                 395                 400
Ala Asp Gln Phe Phe Asn Ala Gln Met Leu Glu Glu Trp Gly Ala Cys
                405                 410                 415
Val Glu Val Ser Arg Gly Asn Trp Pro Asp Ser Pro Ala Leu Glu Arg
                420                 425                 430
Glu Arg Val Val Glu Val Glu Met Val Met Gly Ile Thr Ala Lys
                435                 440                 445
Ala Asp Lys Ile Arg Gln Ser Val Lys Gln Ile Gln Gly Met Ile Gly
        450                 455                 460
Arg Thr Leu Glu Asp Gly Gly Ser Ser Lys Thr Ala Leu Glu Glu Phe
465                 470                 475                 480
Leu Lys Leu His Gly His Ile Met Leu Met Lys Cys
                485                 490
```

<210> SEQ ID NO 4
<211> LENGTH: 496
<212> TYPE: DNA
<213> ORGANISM: Artificial Sequence
<220> FEATURE:
<223> OTHER INFORMATION: Polynucleotide

<400> SEQUENCE: 4

```
ggagaacctc gaagtcaaag aacaacgtgt tcaccatgcc cagcgatggc agcttccgca      60
tcgtcctctt cccgttcccg gcgcagggcc acttctccgc cttcctctcc ctcgccgccc     120
acctccacga cgcccagccc acggccgaca tcaccatcgt ctccaccccg cgcaacgtgg     180
aagacctccg ccgccggtcg agctcccaga cgcggtacct ccggttccac gccctgccgt     240
cgcgccagc cgagcacggc ctgccccgag acatcgagtc gaccgacgcc gtgccgctcc     300
tccacttcat cacgctgttc gaggccaccg agtcgcgctc gctacaggac agcttcgaca     360
gcttcgtccg tgacttgatc accgacgccg gagcggacgg tgccagggtc tgcgtcatcg     420
ccgacccctt cctcgcgtgg acgacagacg tcgcccgccg gcgtggcgcc gcgcacgcca     480
tcttcgtctc ctgcgg                                                    496
```

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5

```
gtaagcttat gcccagcgat ggcagctt                                        28
```

<210> SEQ ID NO 6
<211> LENGTH: 28
<212> TYPE: DNA
<213> ORGANISM: Artificial Sequence
<220> FEATURE:
<223> OTHER INFORMATION: Primer -continued

<400> SEQUENCE: 6
gctctagatc agcatttcat gagcataa                                          28

<210> SEQ ID NO 7
<211> LENGTH: 32
<212> TYPE: DNA
<213> ORGANISM: Artificial Sequence
<220> FEATURE:
<223> OTHER INFORMATION: Primer

<400> SEQUENCE: 7
cagctagcat cgatggagaa cctcgaagtc aa                                     32

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
gcagatctac tagtccgcag gagacgaaga tg                                     32

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
cacccggggg agaacctcga agtcaa                                            26

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
caggatcccc gcaggagacg aagatg                                            26

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
ggcaggccgt tcatttgg                                                     18

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
tgtccgcctt cgccgtaa                                                     18

<210> SEQ ID NO 13

```
<211> LENGTH: 20
<212> TYPE: DNA
<213> ORGANISM: Artificial Sequence
<220> FEATURE:
<223> OTHER INFORMATION: Primer

<400> SEQUENCE: 13
agcttcgtcc gtgacttgat                                               20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gtggatgaga agcccaatgt                                               20

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gaactggtat ggtcaaggct g                                             21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
acacggagct cgttgtagaa g                                             21

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
ccgttcgggt ttgacatcg                                                19

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
gttcttggca cgcatcctct c                                             21

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
```

```
tggtcgtacc acaggtattg tgtt                                          24

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
aaggtcgaga cgaaggatag cat                                           23
```